(12) United States Patent
Liu et al.

(10) Patent No.: US 9,750,841 B2
(45) Date of Patent: Sep. 5, 2017

(54) BIODEGRADABLE MEDICAL ADHESIVE AND PREPARATION METHOD AND USE THEREOF

(71) Applicants: INSTITUTE OF PHARMACOLOGY AND TOXICOLOGY ACADEMY OF MILITARY MEDICAL SCIENCES P.L.A., Beijing (CN); CHENGDU YIPING MEDICAL SCIENCE & TECHNOLOGY CO., LTD., Chengdu (CN)

(72) Inventors: Keliang Liu, Beijing (CN); Liang Xu, Beijing (CN); Qingsong Zhang, Chengdu (CN); Dazhen Cai, Beijing (CN); Qingbin Meng, Beijing (CN)

(73) Assignees: INSTITUTE OF PHARMACOLOGY AND TOXICOLOGY ACADEMY OF MILITARY MEDICAL SCIENCES P.L.A., Beijing (CN); CHENGDU YIPING MEDICAL SCIENCE & TECHNOLOGY CO. LTD, Chengdu (CN)

( * ) Notice: Subject to any disclaimer, the term of this patent is extended or adjusted under 35 U.S.C. 154(b) by 186 days.

(21) Appl. No.: 14/355,827

(22) PCT Filed: Oct. 31, 2012

(86) PCT No.: PCT/CN2012/083787
§ 371 (c)(1),
(2) Date: Aug. 25, 2014

(87) PCT Pub. No.: WO2013/064059
PCT Pub. Date: May 10, 2013

(65) Prior Publication Data
US 2014/0369952 A1    Dec. 18, 2014

(30) Foreign Application Priority Data

Nov. 2, 2011   (CN) .......................... 2011 1 0340675

(51) Int. Cl.
| | |
|---|---|
| A61L 24/06 | (2006.01) |
| C08F 28/02 | (2006.01) |
| A61L 24/00 | (2006.01) |
| C08F 222/32 | (2006.01) |
| C09J 4/00 | (2006.01) |
| A61L 24/04 | (2006.01) |
| C09J 133/14 | (2006.01) |
| C08F 283/02 | (2006.01) |
| C09J 133/20 | (2006.01) |

(52) U.S. Cl.
CPC .......... *A61L 24/06* (2013.01); *A61L 24/0015* (2013.01); *A61L 24/0042* (2013.01); *A61L 24/043* (2013.01); *C08F 222/32* (2013.01); *C08F 283/02* (2013.01); *C09J 4/00* (2013.01); *C09J 133/14* (2013.01); *C09J 133/20* (2013.01); *C08F 2222/324* (2013.01); *C08F 2222/326* (2013.01); *C08L 2312/00* (2013.01)

(58) Field of Classification Search
CPC .......... C08F 2222/328; C08F 2222/324; C08F 2222/326; C08F 2220/286; C08F 2222/322; C08F 222/32; C08F 283/02; A61L 24/0015; A61L 24/0042; C08L 35/04; C08L 2312/00; C09J 133/14; C09J 133/20
See application file for complete search history.

(56) References Cited

U.S. PATENT DOCUMENTS

| | | | |
|---|---|---|---|
| 3,142,698 A | 7/1964 | Halpern et al. | |
| 3,940,362 A | 2/1976 | Overhults | |
| 3,975,422 A | 8/1976 | Buck | |
| 3,995,641 A | 12/1976 | Kronenthal et al. | |
| 4,012,402 A | 3/1977 | Buck | |
| 4,041,061 A | 8/1977 | Buck | |
| 4,041,063 A * | 8/1977 | Buck ..................... | C07C 255/00 558/427 |
| 4,997,861 A * | 3/1991 | Hechenberger ............ | C09J 4/00 523/176 |
| 5,575,997 A | 11/1996 | Leung et al. | |

(Continued)

FOREIGN PATENT DOCUMENTS

| | | |
|---|---|---|
| CN | 87103468 A | 11/1988 |
| CN | 1272797 A | 11/2000 |

(Continued)

OTHER PUBLICATIONS

Office Action and Search Report issued for corresponding Chinese Patent Application No. 01110340675.7 dated Jan. 30, 2014.
Li Jingfeng, Sun Xiping, Preparation and Application of ?-Cyanoacrylate Adhesives, Chinese Journal of Colloid and Polymer, 1999, 17(3): 33-34.

(Continued)

*Primary Examiner* — Anna Falkowitz
(74) *Attorney, Agent, or Firm* — Banner & Witcoff, Ltd.

(57) ABSTRACT

A medical adhesive with good biodegradable performance capable of undergoing crosslinking copolymerization, comprising a mono-alpha-cyanoacrylate and a bis-alpha-cyanoacrylic acid diol ester monomer molecule. The olefinic bonds in the mono-alpha-cyanoacrylate structure are polymerized in the presence of infinitesimal anions to form a solid 3D high polymer; the 3D high polymer is provided with degradation sites on the web-like backbone chain, with clear degradation path and absorbable degradation products. The medical adhesive can be used for wound adhesive, large area wound hemostasia, and visceral and soft tissue wound closure.

11 Claims, 9 Drawing Sheets

(56) References Cited

U.S. PATENT DOCUMENTS

| | | |
|---|---|---|
| 5,582,834 A | 12/1996 | Leung et al. |
| 5,624,669 A | 4/1997 | Leung et al. |
| 6,010,714 A | 1/2000 | Leung et al. |
| 6,217,603 B1 | 4/2001 | Clark et al. |
| 6,512,023 B1 | 1/2003 | Malofsky et al. |
| 6,620,846 B1 | 9/2003 | Jonn et al. |
| 6,699,940 B2 | 3/2004 | Shalaby |
| 7,238,828 B2 | 7/2007 | Liu |
| 7,279,523 B2 | 10/2007 | Ando et al. |
| 7,534,907 B2 | 5/2009 | Liu |
| 2004/0254272 A1 | 12/2004 | Ando et al. |
| 2005/0245966 A1 | 11/2005 | Hammerslag et al. |
| 2006/0147479 A1 | 7/2006 | Atkin et al. |
| 2006/0216266 A1 | 9/2006 | Liu |
| 2007/0224163 A1 | 9/2007 | Liu |
| 2011/0117047 A1* | 5/2011 | Zhang .................. A61L 15/24 424/78.06 |
| 2011/0251318 A1* | 10/2011 | Ishizaki .................. C09J 4/00 524/208 |
| 2012/0197293 A1 | 8/2012 | Smith et al. |

FOREIGN PATENT DOCUMENTS

| | | | |
|---|---|---|---|
| CN | 1329648 A | | 1/2002 |
| CN | 1714107 A | | 12/2005 |
| CN | 101180085 A | | 5/2008 |
| EP | 0990672 A2 | | 4/2000 |
| GB | 1048906 | * | 11/1966 |
| GB | 1048906 A | | 11/1966 |
| JP | 2004-019780 A | | 1/2004 |
| JP | 2006-506149 A | | 2/2006 |
| WO | 2005000985 A2 | | 1/2005 |
| WO | 2010074095 A1 | | 7/2010 |

OTHER PUBLICATIONS

International Search Report mailed Feb. 7, 2012 (PCT/CN2012/083787); ISA/CN.

Xu et al., "A cross-linking strategy provides a new generation of biodegradable and biocompatible cyanoacrylate medical adhesives," J. Mater. Chem. B 4, 4147-55, 2016.

* cited by examiner

 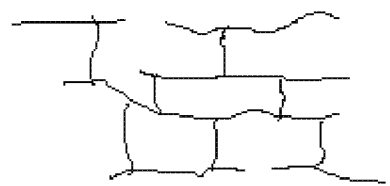
Fig. 1-A  Fig. 1-B

Control    Tested Adhesive

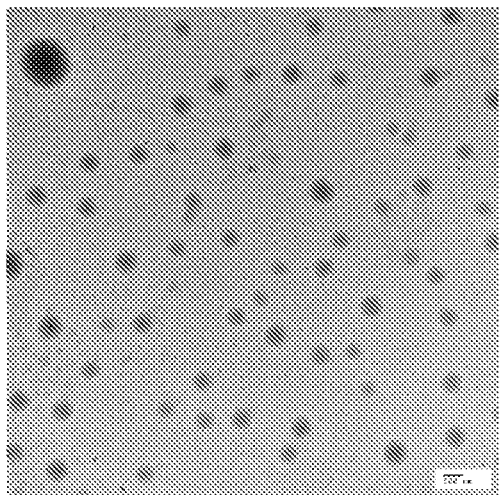
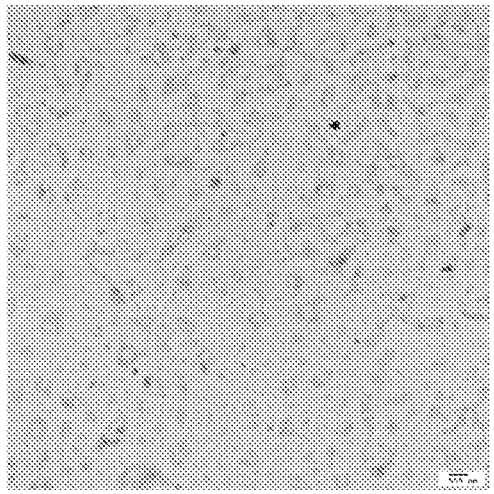
Fig. 7-A　　　　　　　　　　Fig. 7-B
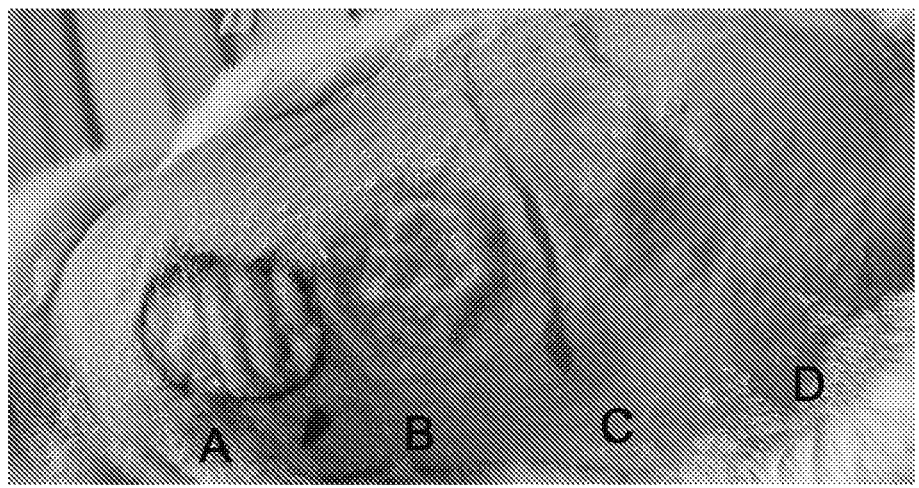
Fig. 8

Fig. 9-A
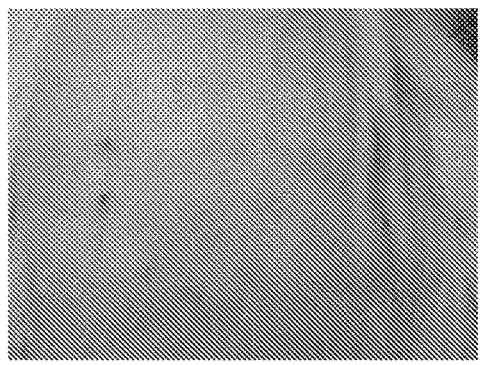
Fig. 9-B
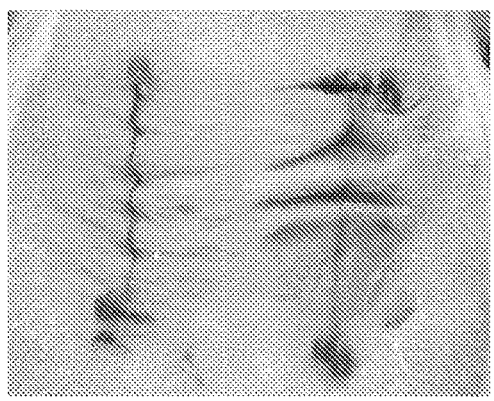
Fig. 10-A
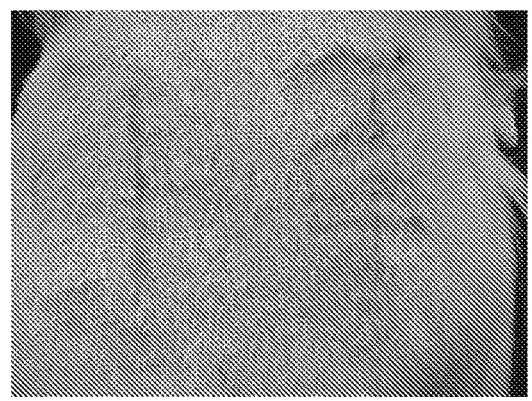
Fig. 10-B
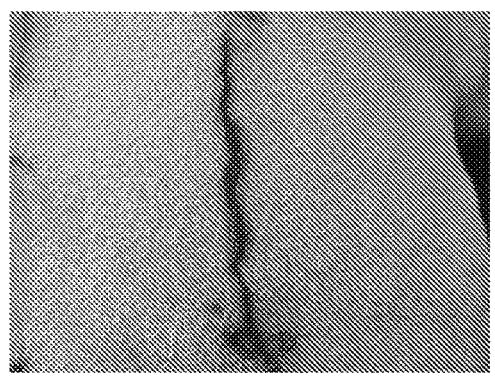
Fig. 11-A
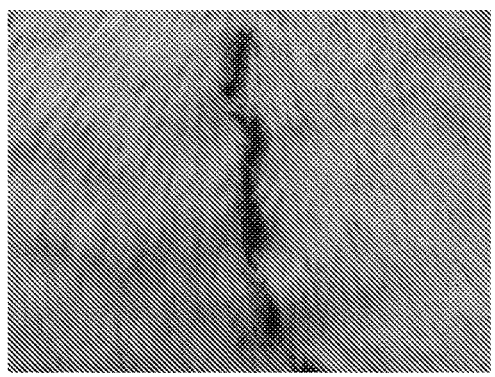
Fig. 11-B

BIODEGRADABLE MEDICAL ADHESIVE AND PREPARATION METHOD AND USE THEREOF

CROSS REFERENCE TO RELATED APPLICATIONS

The present application is a U.S. National Phase filing of International Application No. PCT/CN2012/083787, filed on Oct. 31, 2012, designating the United States of America and claiming priority to Chinese Patent Application No. CN 201110340675.7, filed Nov. 2, 2011. The present application claims priority to and the benefit of all the above-identified applications, and all the above-identified applications are incorporated by reference herein in their entireties.

TECHNICAL FIELD

The present invention relates to a medical adhesive, particularly to a biodegradable medical adhesive. The medical adhesive is biodegradable with non-toxic and absorbable degradation products. It can be used for skin wound adhesion, tissue adhesion, wound hemostasis and the like.

BACKGROUND

The appearance of medical adhesive changes the concept of traditional medicine relying only on stitching wounds. The use of adhesion to replace or assist stitching not only has the advantages including simple operation and no secondary damage to wounds, but also can advantageously apply to or assist the application to soft tissues that are relatively difficult to stitch, for example, liver and pancreas, organs, bones and other parts. In addition, for large superficial hemorrhage, abrasions, burns, battlefield injuries, field damage, intestinal leakage and the like, such medical adhesive can also form a protective film over wounds by means of coverage hemostasis, so as to achieve the purpose of hemostasis and prevention from external infection.

Alkyl $\alpha$-cyanoacrylate is the most widely used type of medical adhesive. In its structure, $\alpha$carbon atom is linked to a cyano group and an ester group, so the double bond has a very low electron cloud density, and it has a very strong electron-withdrawing property, and can generate instantaneous intermolecular polymerization under the action of infinitesimal anions (amino group, hydroxyl group, trace weak basic material such as steam and the like on the surface of biological tissues). In general, alkyl $\alpha$-cyanoacrylate as monomer is in liquid state, and, after being used by spraying or smearing to contact with human tissue, it rapidly polymerizes (less than 30 seconds) to cure, resulting in the desired adhesion or seal strength. In 1959, the first cyanoacrylate adhesive Eastman910 (methyl $\alpha$-cyanoacrylate) was marketed for skin adhesion and hemostasis. Subsequently, a number of cyanoacrylate adhesives were synthesized in various countries, for example, AU-CRYLATE (the main component thereof being n-/iso-butyl $\alpha$-cyanoacrylate) in USA, HISTOACRYL BLUE (the main component thereof being n-butyl $\alpha$-cyanoacrylate) in Germany.

The research and production of medical adhesives have been carried out in China since 1962, mainly including FAL (n-butyl/n-octyl $\alpha$-cyanoacrylate), butyl $\alpha$-cyanoacrylate, isobutyl $\alpha$-cyanoacrylate, n-octyl $\alpha$-cyanoacrylate and the like. These commercialized products have been widely used in clinical applications, but they still have some drawbacks. For example, the resulting polymer has relatively poor flexibility, and the resulting adhesive bond are relatively hard, which are unfavorable for the use in soft organs such as tissue and skin; the degradability is poor due to that single $\alpha$-cyanoacrylate polymerizes to form a linear polymer, whose linear backbone chain obtained by polymerization of carbon-carbon double bond has a relatively high level of carbon-carbon bond energy, and is difficult to break, so this type of polymer degrades very slowly, and the presence thereof at the wound site for a long time may lead to foreign body reaction, and may cause new inflammation and even impede further wound healing, to thereby reduce the practical value thereof as a surgical adhesive/sealant.

Several patents reported modifications of the ester chain portion, including introduction of more ester linkage sites in the structure, to accelerate the degradation of side chain. U.S. Pat. No. 3,995,641, as filed by Kronenthal et al, discloses a carbalkoxyalkyl cyanoacrylate adhesive, which can form an absorbable polymer in mammalian tissue. Chinese patent CN101180085A discloses a cyanoacrylate structure containing a plurality of ester linkages and spacer groups in its side chain to accelerate degradation.

Although the modifications on side chain in these documents accelerate the degradation of side chain ester, these degradation modes, in fact, all deal with the degradation of the polymer side chain, while the linear carbon-carbon backbone chain of the polymer is still difficult to be degraded and absorbed. Thus, there is still a need to develop a medical adhesive whose polymer backbone chain has better biodegradability and biocompatibility.

BRIEF SUMMARY

The present invention relates to a type of medical adhesives which can undergo crosslinking copolymerization and has good biodegradability. The biodegradability of the medical adhesives has been greatly improved as compared with the existing cyanoacrylate adhesives.

Specifically, such type of crosslinked biodegradable medical adhesive is a multi-component mixture, wherein the polymer matrix includes two components or more components, i.e., at least comprising a mono-$\alpha$-cyanoacrylate and a bis-$\alpha$-cyanoacrylic acid diol ester. The formulation of the polymer matrix can be described as follows: a medical adhesive, characterized in comprising: a mono-$\alpha$-cyanoacrylate and a bis-$\alpha$-cyanoacrylic acid diol ester; wherein in the medical adhesive the weight ratio of the mono-$\alpha$-cyanoacrylate to the bis-$\alpha$-cyanoacrylic acid diol ester is 1-9.9:0.1-9; preferably the weight ratio of the mono-$\alpha$-cyanoacrylate to the bis-$\alpha$-cyanoacrylic acid diol ester is 3-7:3-7; and particularly preferably the weight ratio of the mono-$\alpha$-cyanoacrylate to the bis-$\alpha$-cyanoacrylic acid diol ester is 1:1.

Further, preferably the alkyl mono-$\alpha$-cyanoacrylate is at least one member selected from the group consisting of n-butyl $\alpha$-cyanoacrylate and n-octyl $\alpha$-cyanoacrylate, and the bis-$\alpha$-cyanoacrylic acid diol ester is bis-$\alpha$-cyanoacrylic acid PEG2000 ester.

Preferably the weight ratio of n-butyl $\alpha$-cyanoacrylate and/or n-octyl $\alpha$-cyanoacrylate to bis-$\alpha$-cyanoacrylic acid PEG2000 ester is 3-7:3-7; and particularly preferably the weight ratio of n-butyl $\alpha$-cyanoacrylate to bis-$\alpha$-cyanoacrylic acid PEG2000 ester is 1:1.

Optionally, the medical adhesive further comprises a pharmaceutically acceptable excipient.

The structure of the mono-$\alpha$-cyanoacrylate is represented by Formula I:

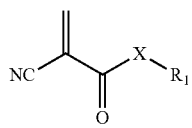

wherein $R_1$ is, but not limited to, straight and branched alkyl group having 1-30 carbon atoms, such as ethyl, n-butyl, n-octyl, iso-butyl, iso-octyl; straight and branched alkyl group having 1-30 carbon atoms substituted with acyloxy group, haloalkyl group, alkoxy group, halogen atom, cyano group and the like; straight and branched alkenyl group having 1-30 carbon atoms; straight and branched alkynyl group having 1-30 carbon atoms; cycloalkyl group, aralkyl group, alkylaryl group, or aryl group, preferably n-butyl, n-octyl, iso-butyl, or iso-octyl.

X can be an oxygen atom, or a nitrogen atom. X—$R_1$ can also represent ethylene glycol group, polyethylene glycol (PEG) group, polyethylene glycol monomethyl ether (mPEG) group, amino PEG group and the like.

The structure of the bis-α-cyanoacrylic acid diol ester is represented by Formula II:

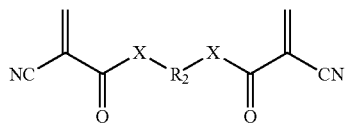

wherein X—$R_2$—X represents a middle molecular fragment sandwiched between two α-cyano acryloyl moieties, whose molecular prototype is selected from the molecular structures that not only have good biocompatibility, but also are degradable in vivo, and have a wide application in the field of bio-medicine, food and the like, and it may be, but not limited to, small molecule diols, polyethylene glycol (PEG), amino PEG, polylactic acid (PLA), polyglycolic acid (PGA), lactic acid-glycolic acid copolymer (PLGA), copolymers containing polyhydroxy acid and polyglycol compounds such as PLA-PEG-PLA block copolymers and PGA-PEG-PGA block copolymers, preferably PEG and small molecule diols.

X can be an oxygen atom, or a nitrogen atom.

BRIEF DESCRIPTION OF THE DRAWINGS

FIG. 1-A, a schematic diagram of a linear polymer obtained by polymerization of mono-α-cyanoacrylate;

FIG. 1-B, a schematic diagram of a three-dimensional polymer obtained by polymerization of monomers comprising bis-α-cyanoacrylic acid diol ester;

FIG. 7-A, transmission electron microscope image of n-butyl cyanoacrylate, scale 500 nm;

FIG. 7-B, transmission electron microscope image of the formulated adhesive (J01) in Example 1, scale 500 nm;

FIG. 8, comparison results of flexibility of adhesives on the back of rats;

FIG. 9-A and FIG. 9-B, skin incision model test of rats, the formulated adhesive in Example 1 being applied on the left wound, and n-butyl cyanoacrylate being applied on the right wound, FIG. 9-A showing the experimental results of rats 1 day after operation, and FIG. 9-B showing the experimental results of rats 7 days after operation;

FIG. 10-A and FIG. 10-B, skin incision model test of guinea pigs, the formulated adhesive in Example 1 being applied on the left wound, and n-butyl cyanoacrylate being applied on the right wound, FIG. 10-A showing the test results of guinea pigs 1 day after operation, and FIG. 10-B showing the test results of guinea pigs 7 days after operation;

FIG. 11-A and FIG. 11-B, skin incision model control of guinea pigs, the wound being untreated, FIG. 11-A showing the results of guinea pigs 1 day after operation, and FIG. 11-B showing the results of guinea pigs 7 days after operation;

DETAILED DESCRIPTION

Figure 2:
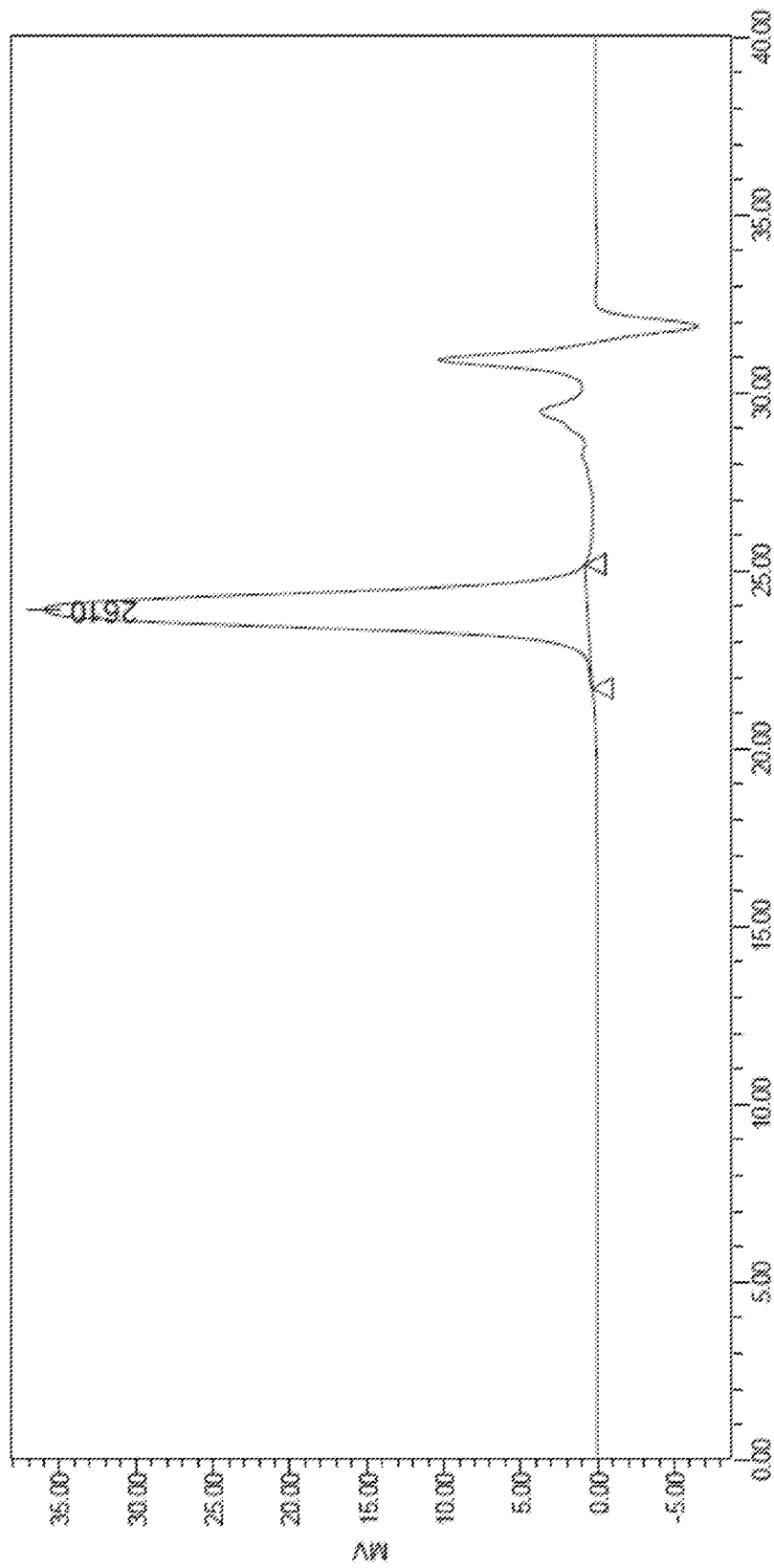
FIG. 2, a GPC diagram of PBS degradation solution of polymer No. J01.

As discussed above, the present invention relates to a type of medical adhesives which can undergo crosslinking copolymerization and has good biodegradability. The biodegradability of the medical adhesives has been greatly improved as compared with the existing cyanoacrylate adhesives.

Specifically, such type of crosslinked biodegradable medical adhesive is a multi-component mixture, wherein the polymer matrix includes two components or more components, i.e., at least comprising a mono-α-cyanoacrylate and a bis-α-cyanoacrylic acid diol ester. The formulation of the polymer matrix can be described as follows: a medical adhesive, characterized in comprising: a mono-α-cyanoacrylate and a bis-α-cyanoacrylic acid diol ester; wherein in the medical adhesive the weight ratio of the mono-α-cyanoacrylate to the bis-α-cyanoacrylic acid diol ester is 1-9.9:0.1-9; preferably the weight ratio of the mono-α-cyanoacrylate to the bis-α-cyanoacrylic acid diol ester is 3-7:3-7; and particularly preferably the weight ratio of the mono-α-cyanoacrylate to the bis-α-cyanoacrylic acid diol ester is 1:1.

Further, preferably the alkyl mono-α-cyanoacrylate is at least one member selected from the group consisting of n-butyl α-cyanoacrylate and n-octyl α-cyanoacrylate, and the bis-α-cyanoacrylic acid diol ester is bis-α-cyanoacrylic acid PEG2000 ester.

Preferably the weight ratio of n-butyl α-cyanoacrylate and/or n-octyl α-cyanoacrylate to bis-α-cyanoacrylic acid PEG2000 ester is 3-7:3-7; and particularly preferably the weight ratio of n-butyl α-cyanoacrylate to bis-α-cyanoacrylic acid PEG2000 ester is 1:1.

Optionally, the medical adhesive further comprises a pharmaceutically acceptable excipient.

The structure of the mono-α-cyanoacrylate is represented by Formula I:

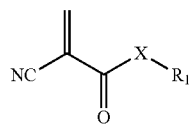

wherein $R_1$ is, but not limited to, straight and branched alkyl group having 1-30 carbon atoms, such as ethyl, n-butyl, n-octyl, iso-butyl, iso-octyl; straight and branched alkyl group having 1-30 carbon atoms substituted with acyloxy group, haloalkyl group, alkoxy group, halogen atom, cyano group and the like; straight and branched alkenyl group having 1-30 carbon atoms; straight and branched alkynyl group having 1-30 carbon atoms; cycloalkyl group, aralkyl group, alkylaryl group, or aryl group, preferably n-butyl, n-octyl, iso-butyl, or iso-octyl.

X can be an oxygen atom, or a nitrogen atom. $X-R_1$ can also represent ethylene glycol group, polyethylene glycol (PEG) group, polyethylene glycol monomethyl ether (mPEG) group, amino PEG group and the like.

The structure of the bis-α-cyanoacrylic acid diol ester is represented by Formula II:

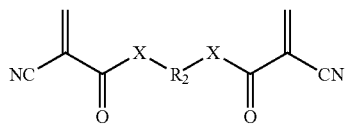

II wherein $X-R_2-X$ represents a middle molecular fragment sandwiched between two α-cyano acryloyl moieties, whose molecular prototype is selected from the molecular structures that not only have good biocompatibility, but also are degradable in vivo, and have a wide application in the field of bio-medicine, food and the like, and it may be, but not limited to, small molecule diols, polyethylene glycol (PEG), amino PEG, polylactic acid (PLA), polyglycolic acid (PGA), lactic acid-glycolic acid copolymer (PLGA), copolymers containing polyhydroxy acid and polyglycol compounds such as PLA-PEG-PLA block copolymers and PGA-PEG-PGA block copolymers, preferably PEG and small molecule diols.

X can be an oxygen atom, or a nitrogen atom.

When the prototype of the middle molecular fragment represented by $X-R_2-X$ is a small molecule diol (which corresponds to that X is an oxygen atom), the diol can be a hydrocarbyl diol or a substituted hydrocarbyl diol, and $R_2$ can be, but not limited to, straight and branched hydrocarbyl group having 1-30 carbon atoms; straight and branched hydrocarbyl group having 1-30 carbon atoms substituted with acyloxy group, haloalkyl group, alkoxy group, halogen atom, cyano group and the like; straight and branched alkenyl group having 1-30 carbon atoms; straight and branched alkynyl group having 1-30 carbon atoms; cycloalkyl group, aralkyl group, alkylaryl group, or aryl group. The prototype of the middle molecular fragment represented by $X-R_2-X$ is preferably ethylene glycol, butanediol, or octanediol.

When the prototype of the middle molecular fragment represented by $X-R_2-X$ is polyethylene glycol (which corresponds to that X is an oxygen atom), amino polyethylene glycol (which corresponds to that X is a nitrogen atom), the structure of $R_2$ is represented by Formula III:

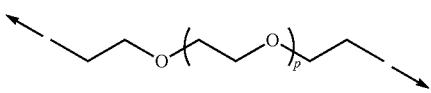

III wherein p can be an integer of 0 to 100, preferably 5 to 50.

When the prototype of the middle molecular fragment represented by $X-R_2-X$ is polylactic acid (PLA), polyglycolic acid (PGA), lactic acid-glycolic acid copolymer (PLGA), the structure of $R_2$ is represented by Formula IV:

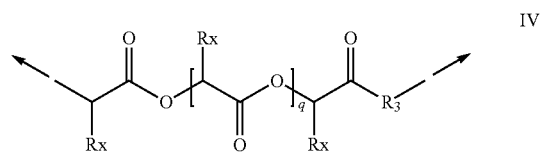

IV wherein, $R_x$ can arbitrarily be —H or —$CH_3$ in the chain, without being restricted by the repeating structural units; when $R_x$ is —H, the fragment is PGA; when $R_x$ is —$CH_3$, the fragment is PLA; when $R_x$ are both —H and —$CH_3$, the fragment is PLGA; q can be an integer from 0 to 100, preferably from 5 to 50; $R_3$ is a linker arm, including, but not limited to, amino alcohol molecules such as amino pentyl alcohol, amino hexyl alcohol, ethylene glycol, butanediol, PEG and the like.

When the prototype of the middle molecular fragment represented by $X-R_2-X$ is a block copolymer of polyhydroxy acid and polyglycol compounds, the structure of $R_2$ is represented by Formula V:

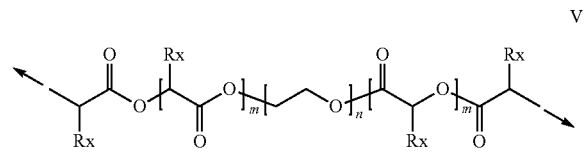

V wherein, $R_x$ can arbitrarily be —H or —$CH_3$ in the chain, without being restricted by the repeating structural units; m can be from 0 to 50, preferably from 1 to 10; n can be from 1 to 100, preferably from 1 to 10; wherein the polyethylene glycol (PEG) fragment

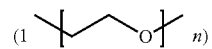

can be replaced with a similar diol or its polymer (polyether), including, but not limited to, propanediol, butanediol, silanediol, polypropylene glycol, polydimethylsiloxane and the like, and can also be replaced with a similar diamine or its polymer (polyamine), including, but not limited to ethylenediamine, propylenediamine and the like, which is linked via amide linkage at both ends.

In the medical adhesive of the present invention, the mono-α-cyanoacrylate is n-butyl α-cyanoacrylate; the bis-α-cyanoacrylic acid diol ester is bis-α-cyanoacrylic acid PEG2000 ester; and the weight ratio of n-butyl α-cyanoacrylate to bis-α-cyanoacrylic acid PEG2000 ester is 1:1.

In the medical adhesive of the present invention, the formulations in weight ratio is selected from the following formulations:

1. bis-α-cyanoacrylic acid PEG2000 ester:n-butyl α-cyanoacrylate 1:1;
2. bis-α-cyanoacrylic acid PEG2000 ester:n-butyl α-cyanoacrylate 1:5;

3. bis-α-cyanoacrylic acid PEG2000 ester:n-butyl α-cyanoacrylate 9.1:90.9;

4. bis-α-cyanoacrylic acid PEG2000 ester:n-octyl α-cyanoacrylate 1:1;

5. bis-α-cyanoacrylic acid PEG2000 ester:n-octyl α-cyanoacrylate 1:5;

6. bis-α-cyanoacrylic acid PEG2000 ester:n-octyl α-cyanoacrylate 9.1:90.9;

7. bis-α-cyanoacrylic acid butanediol ester:n-butyl α-cyanoacrylate 1:5;

8. bis-α-cyanoacrylic acid octanediol ester:n-butyl α-cyanoacrylate 1:5;

9. bis-α-cyanoacrylic acid butanediol ester:n-octyl α-cyanoacrylate 1:5;

10. bis-α-cyanoacrylic acid octanediol ester:n-octyl α-cyanoacrylate 1:5;

11. bis-α-cyanoacrylic acid (PLA-PEG-PLA) ester:n-octyl α-cyanoacrylate 1:1;

12. bis-α-cyanoacrylic acid diethylene glycol ester:n-butyl α-cyanoacrylate 1:1;

13. bis-α-cyanoacrylic acid tetraethylene glycol ester:n-octyl α-cyanoacrylate 1:1;

14. bis-α-cyanoacrylic acid PEG600 ester:n-butyl α-cyanoacrylate 1:1;

15. bis-α-cyanoacrylic acid PEG1000 ester:n-octyl α-cyanoacrylate 1:1;

16. bis-α-cyanoacrylic acid PEG4000 ester:n-octyl α-cyanoacrylate 1:1; and 17. bis-α-cyanoacrylic acid PEG2000 ester:n-butyl α-cyanoacrylate 5:1.

The medical adhesive of the present invention can further comprise, but not limited to, a combination of one or more adjuvants, such as thickeners, stabilizers, thermal initiators and/or photoinitiators and accelerators capable of initiating crosslinking, colorants, plasticizers, preservatives, heat dissipating agents, biocompatible agents, and fiber reinforced materials. In addition, the medical adhesive, as required, can also comprise one or more therapeutic agents or biological agents. Chinese patent CN101180085A describes the types of these adjuvants, which is incorporated in its entirety herein by reference.

Plasticizers can confer flexibility on the polymer formed by the monomer. Plasticizers should not include water, and do not significantly affect the stability or polymerization of the monomer. Examples of suitable plasticizers include, but not limited to, polyethylene glycol ester, end-capped polyester, butyl stearate, lauric acid, dioctyl glutarate, triglyceride, dioctyl oxalate, triethyl phosphate, acetyl tributyl citrate and the like.

Thickeners can increase elongation and toughness, including, but not limited to, polycyanoacrylate, polylactic acid, polyglycolic acid, polycaprolactone, polyacrylic acid alkyl ester, polymethacrylic acid alkyl ester and the like.

Preservatives include, but not limited to, those that are conventionally used and do not initiate polymerization of the monomer, such as potassium sorbate, sodium benzoate, sorbic acid, chlorocresol and the like.

Heat dissipating agents include liquids miscible with the monomer, which can evaporate during the polymerization, and release heat from the composition. U.S. Pat. No. 6,010,714 discloses suitable heat dissipating agents, such as ethyl ether, acetone, pentane and the like, which is incorporated in its entirety herein by reference.

Fiber reinforced material includes, but not limited to, natural rubber or synthetic rubber to enhance impact resistance of the composition, such as styrene, acrylonitrile and the like.

Stabilizers include anionic stabilizers and free radical stabilizers, the former including metaphosphoric acid, maleic acid, maleic anhydride, alkyl sulfonic acid, phosphorus pentoxide, iron (III) chloride, antimony oxide, 2,4,6-trinitrophenol, thiol, alkyl sulfonyl, alkyl sulfone, alkyl sulfoxide, alkyl sulfite, sultone, sulfur dioxide, sulfur trioxide and the like, and the latter including hydroquinone, catechol and derivatives thereof. Stabilizers serve the purpose of inhibiting polymerization of the monomer during storage. The presence of stabilizer should not exert any adverse effect on the use and absorption of the composition. U.S. Pat. No. 6,512,023 discloses suitable stabilizers, which is incorporated in its entirety herein by reference.

Colorants are dyes, pigments and the like. Examples thereof include PGA microfibrils, collagen microfibrils, cellulose microfibrils, olefinic microfibrils and the like. Patent CN1714107A discloses a type of dyes that can change color with curing of cyanoacrylate, such as bromocresol green, methyl yellow, methyl red, pentamethoxy red, which is incorporated in its entirety herein by reference.

The medical adhesive of the present invention can optionally comprise one or more biological agents or therapeutic agents. These biological agents/therapeutic agents include, but not limited to, anti-inflammatory analgesics; sedatives; local anesthetics; non-steroidal anti-inflammatory agents; antiallergic agents; anti-ulcer agents; antibiotics; antimicrobial agents; antiviral agents; antifungal agents; immunity inhibitors; naturally derived proteins or genetically engineered proteins; polysaccharides; glycoproteins or lipoproteins; oligonucleotides; polypeptide drugs; antibodies; antigens; chemotherapeutics; coagulant agents and hemostatic agents, such as prothrombin, thrombin, fibrinogen, fibrin, fibronectin, coagulation factors, tissue factors, collagen, gelatin, vasopressin, plasminogen activator inhibitors, platelet activators and synthetic peptides having hemostatic activity.

Biocompatible agents also refer to formaldehyde concentration-reducing agents or formaldehyde scavengers, which can alleviate the release of formaldehyde as a byproduct during in situ biodegradation of the polymer, including, but not limited to, sodium bisulfite and the like. U.S. Pat. Nos. 6,010,714, 5,624,669, 5,582,834, and 5,575,997 disclose compounds and compositions capable of reducing the level of formaldehyde, which are incorporated in their entirety herein by reference.

Initiators or accelerators include, but not limited to, molecules having nucleophilic functional groups, organics or inorganics or mixtures thereof, such as amino, quaternary amine, hydroxyl, thiol, phosphorus-containing compounds, as well as others such as $NaHCO_3$, $Na_2CO_3$, sodium phosphate. U.S. Pat. No. 6,620,846B1 discloses suitable initiators and accelerators, which is incorporated in its entirety herein by reference.

The initiators or accelerators may be applied to tissue prior to the monomer composition, or may be applied to the monomer composition when the monomer composition is applied to tissue.

The medical adhesive provided in the present invention is in a solid form at room temperature, and can rapidly undergo crosslinking copolymerization under the action of infinitesimal anions (—OH, —$NH_2$ in blood, body fluids, tissues, skin) to form a cured polymer film, and meanwhile adhere the tissue in contact therewith together, with the adhesive strength greater than the wound tension. The cured film plays a role in the coverage hemostasis and can avoid further bacterial infection and accelerate healing. In view of its good degradation rate, the medical adhesive provided in the present invention can be used for wound adhesion, large-area wound hemostasis, as well as wound closure of visceral and soft tissues and the like, and thus is applicable to surgery in the human body, for example, hemostasis, adhesion, coverage, leak stopping, hard tissue fixation in the surgery such as cardiothoracic, urology, neurosurgery, oncological surgery, general surgery (hepatobiliary, pancreas, stomach, intestines), bone surgery, stomatology, otorhinolaryngology and the like.

Furthermore, such α-cyanoacrylate molecule composition can also be used to develop tissue engineered scaffold material. The tissue engineered scaffold material serves the purpose of providing a three-dimensional scaffold for constructing tissue cells, which is favorable for cell adhesion, proliferation and differentiation, and provides a suitable external environment for cell growth. It needs to meet the following conditions: good biocompatibility, no significant toxicity, inflammation and immune rejection; degradability and appropriate rate of degradation; suitable pore size, high porosity and pore morphology in communication; structural strength to match mechanical properties of the implantation site tissue; easy to be processed into the desired two- or three-dimensional structure, and the like. The α-cyanoacrylate adhesive provided in the present invention just has the characteristics including good biocompatibility, mechanical properties, adjustability in property, and easy to process, can satisfy the purpose of such biodegradable tissue engineered scaffold material, and can form by polymerization a solid form with certain strength and support to meet the requirements of tissue engineered scaffold material, and can also gradually self-degrade as tissue grows, resulting in non-toxic and absorbable degradation products.

The preparation, storage and use methods of the medical adhesive of the present invention are as follows:

(1) Sterilization: all the vessels used are soaked with acid (diluted hydrochloric acid or diluted sulfuric acid) and washed, and then sterilized at a high temperature; the liquid alkyl mono-α-cyanoacrylate is subjected to aseptic filtration through an organic microporous filtration membrane with a suitable pore size, preferably an organic microporous filtration membrane with a pore size of 0.22 um (purchased from Solarbio Co. Ltd., model: pore size 0.22 um, this type of filtration membrane is manufactured in many factories, which is universal); the compound can also be sterilized by means of autoclave sterilization or radiation sterilization.

(2) Compounding the adhesive: under dry conditions, 10-99 wt % of mono-α-cyanoacrylate and 1-90 wt % of bis-α-cyanoacrylic acid diol ester, and adjuvants (if present) are weighed, and added in turn to a vessel, and mechanically stirred or shaken with a vortex shaker for 10 min. An external heating mode (no more than 80° C.) can be used simultaneously to promote dissolution. After all the components are dissolved and uniformly mixed, it shall give a colorless or yellowish transparent liquid, namely the medical adhesive of the present invention.

(3) Storage: the medical adhesive obtained in step (2) is subpackaged in vessels in a dry environment, followed by filling the vessels with an inert gas such as nitrogen and argon; then, the vessels are sealed, and stored in a refrigerator (4° C. or lower); the adhesive can be stored stably for not less than two months.

(4) Use: the medical adhesive is taken from the low temperature environment and returned to room temperature; and the medical adhesive should be in liquid state. At this time, the compounds comprised therein are all in the form of non-polymerized monomers. When used, the liquid can be applied to wound or tissue site by means of smearing, spraying, dropping and the like, which can rapidly polymerize to form a solid polymer and generate adhesion.

The present invention further relates to use of the medical adhesive for wound adhesion, hemostasis, wound closure of visceral and soft tissues, coverage, leak stopping, hard tissue fixation, and for the preparation of tissue engineered materials.

The present invention further relates to a method for wound treatment, wherein the wound treatment includes wound adhesion, hemostasis, wound closure of visceral and soft tissues, coverage, leak stopping, hard tissue fixation and the like, the method comprising contacting the medical adhesive according to any one of claims 1-8 with the wound site to be treated.

The present invention further relates to a medical adhesive polymer, said polymer being obtained by crosslinking copolymerization of the medical adhesive according to any one of claims 1-8 under the action of infinitesimal anions, wherein, preferably, the infinitesimal anions are —OH, —NH$_2$ in blood, body fluids, tissues, skin. The main polymer matrix component in the currently marketed medical adhesive products is mono-α-cyanoacrylate molecule, whose linear polymer backbone chain is very difficult to degrade. The earliest report about the molecular structure of bis-α-cyanoacrylic acid diol esters occurred in 1960s. As generally considered, its polymer had a relatively high degree of crosslinking, mechanical strength and hardness, and was stable in moisture environment. As described in British Patent No. GB1048906A, U.S. Pat. Nos. 3,142,698, and 6,699,940 and the like, the diester middle fragments include polyethylene glycol (PEG), neopentyl glycol, polyester, polycarbonate, polyether, polysiloxane, polyolefin, polyalkyne and the like. In this paper, the block copolymer of polyglycolic acid and polyglycol compound is set forth for the first time.

The most significant advantage of the new type of medical adhesive provided in the present invention lies in that it has good biodegradability. The good biodegradability of the medical adhesive is achieved by using a combination of the mono-α-cyanoacrylate and bis-α-cyanoacrylic acid diol ester as the polymer matrix component, wherein the latter acts as a crosslinking agent, and screening suitable type of the mono-α-cyanoacrylate and bis-α-cyanoacrylic acid diol ester, and a suitable ratio thereof.

The use of suitable mono-α-cyanoacrylate and bis-α-cyanoacrylic acid diol ester as the copolymer matrix to carry out crosslinking copolymerization is one of the characteristics of such medical adhesive.

Being different from the polymer having a linear backbone chain (as shown in FIG. 1-A) obtained by linear polymerization of mono-α-cyanoacrylate, when the polymer matrix comprises bis-α-cyanoacrylic acid diol esters, since the monomer molecules include two polymerizable ethylenic bonds, and have a molecular functionality of 4, the polymer matrix undergoes crosslinking copolymerization to form a 3D polymer. Being restricted by its structure and the mode of crosslinking copolymerization, the polymer matrix undergoes chain growth in a three-dimensional multi-point polymerization mode, and has a rapid gelation rate, and a low degree of linear polymerization due to polymerization of double bond. The extended carbon chain generated by polymerization of carbon-carbon bonds, together with the R$_2$ moiety in the bis-α-cyanoacrylic acid diol ester, constitutes a web-like backbone chain in space (as shown in FIG. 1-B).

The second characteristic of the medical adhesive provided in the present invention is that it has good backbone chain degradability.

Being different from the non-degradability of the linear carbon-carbon backbone chain of poly(mono-α-cyanoacrylate), the $R_2$ moiety in the bis-α-cyanoacrylic acid diol ester participates in the formation of web-like backbone chain. The crosslinking points of the web-like, i.e., the connection modes of the $R_2$ moiety with the carbon-carbon chain of polycyanoacrylate, are ester bond and amide bond structures, especially ester bond, which has a relatively low bond energy, and is easy to degrade. Thus, the overall spatial web-like backbone chain comprising these sites can be destroyed through said sites, i.e., these sites are degradation sites of the polymer web-like backbone chain. In addition, likewise, the $R_2$ moiety can also be designed to comprise in itself the sites including ester bond, amide bond, siloxane bond and the like, to achieve the purpose of degrading the web-like backbone chain. When the web-like structure of the polymer is destroyed by degradation, the polymer is actually decomposed into polycyanoacrylate carbon-carbon backbone chain moiety and $R_2$ backbone chain moiety, and some other degradation fragments. Meanwhile, as described in the first characteristic, due to the limitation caused by the steric hindrance of diester, the degree of linear polymerization of double bonds, i.e., the degree of extension of carbon chain, is much smaller than that of single mono-α-cyanoacrylate, which is to say that the decomposed polycyanoacrylate carbon-carbon chain has a relatively small molecular weight, so it can be absorbed and discharged. In other words, such polymer is biodegradable, and absorbable. The good degradability of the product will be further described in combination with the test data in the following Examples 4, 5, 6 and 7.

The third characteristic is that the degradation fragments are non-toxic and absorbable, i.e., they have good biocompatibility.

In the present invention, the molecular structures, which not only have good biocompatibility, but also can be degraded in vivo, and also have wide applications in the fields including bio-medicine, food and the like, are selected to act as the $R_2$ moiety in bis-α-cyanoacrylic acid diol ester. For example, PLA and PGA involved have been approved by US Food and Drug Administration (FDA) to be widely used as medical sutures, temporary stents and drug controlled release carrier. PEG is a polymer which is featured with good biocompatibility, nontoxic to human body, stable in aqueous solution, quite low immunogenicity and antigenicity, and easy to be discharged. It is also one of the very few synthetic polymers that have been approved by the FDA to be used for medicinal injection in vivo. The degradation products of the adhesive bond obtained in the present invention include short segments of polycyanoacrylates, glycolic acid, lactic acid, PLA, PGA, PEG and the like. These fragments are relatively nontoxic, and biocompatible, and can be discharged after glomerular filtration.

The fourth characteristic is the adjustability.

As described above, the $R_2$ moiety in the diester molecule participates in the formation of the web-like backbone chain of the three-dimensional structure. The length and structure of the $R_2$ moiety, and the content of the bis-α-cyanoacrylic acid diol ester will all directly influence the morphology of the web-like. Therefore, by adjusting the length and type of the $R_2$ moiety in the bis-α-cyanoacrylic acid diol ester, and the ratio of diester/monoester, it is possible to adjust the degree of polymerization of the entire polymer, change the length of the extended carbon-carbon chain, change the speed of polymerization, change the size of the spatial web-like, change the flexibility of the polymer and the like. More importantly, the medical adhesive should have such a good degradability that the adhesive bond is gradually and completely degraded as the wound heals, i.e., it not only requires a certain time to adhere the wound, but also needs to avoid a long-term presence resulting in foreign body reaction. Therefore, the adjustability also refers to adjusting the degradation rate of the polymer. Furthermore, the physical properties and the like of the entire adhesive bond can also be improved by virtue of the property of the $R_2$ moiety. For example, PEG-1000, PEG-1500 are often used as a matrix or lubricant, softener in medicine, textile and cosmetics industries, and as a dispersant in paint industry, to improve water dispersibility, flexibility and the like of resin. When they are incorporated in an appropriate manner into the $R_2$ moiety in the bis-α-cyanoacrylic acid diol ester, it is possible to confer the adhesive bond with preferable flexibility. In Examples 8 and 9 below, the use as a copolymer matrix of bis-α-cyanoacrylic acid diol ester containing PEG2000 as middle segment results in a medical adhesive having good flexibility.

The present invention has the following advantages: to provide a medical adhesive containing mono-/bis-α-cyanoacrylates as polymer matrix, which, in addition to the function of conventional medical adhesive, has the greatest feature that the polymer is biodegradable, the degradation product is nontoxic and absorbable, and moreover, through optimization of the structure and formulation, the physical/chemical properties including flexibility, degradation rate and the like of the adhesive bond can be adjusted. Due to its good degradability, this type of medical adhesive can be used more safely, will not cause enrichment to thereby affect wound healing, and will not be present for a long time to thereby cause foreign body reaction. Thus, the use of this type of medical adhesive in vivo, in particular the use in some tissues and organs, is safer. In addition, this type of medical adhesive can be used for preparing tissue engineered materials.

EXAMPLES

The embodiments of the present invention will be described in detail by combining the following examples. However, as will be understood by a person skilled in the art, the following examples are only used to illustrate the present invention, and should not be regarded to limit the scope of the present invention. Where the concrete conditions are not specified, the examples are carried out under conventional conditions or under conditions as recommended by the manufacturer. Where the manufacturer is not specified, all the reagents or the instruments are conventional products that are commercially available.

Preparation Example 1

Synthesis of bis-α-cyanoacrylic Acid PLA-PEG-PLA Ester

The syntheses of bis-α-cyanoacrylic acid esters are substantially similar. A method similar to those disclosed in the references (U.S. Pat. Nos. 3,975,422, 4,012,402, 4,041,061) is used for the syntheses. It is illustrated in this example by taking bis-α-cyanoacrylic acid PLA-PEG-PLA ester as an example.

Bis-α-cyanoacrylic acid PLA-PEG-PLA ester has the following structure:

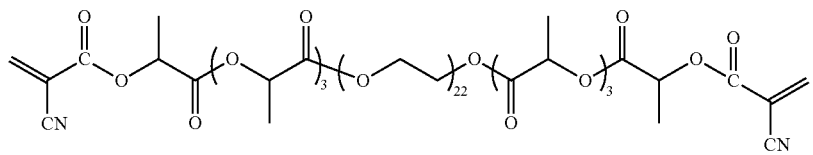

wherein the specific middle segment PLA-PEG-PLA block copolymer (1-1) was synthesized by using the following process:

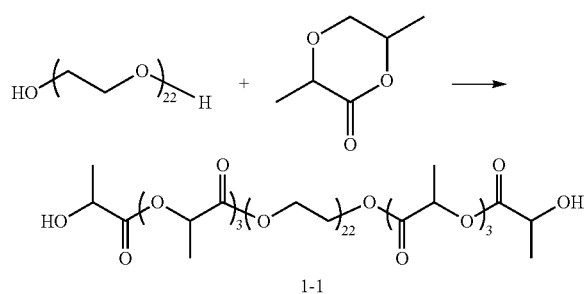

10.13 g (10.13 mmol) of PEG1000 and 10.37 g (72 mmol) of lactide were added to a reaction flask, and heated to 70° C. to melt the solid. The reaction flask was evacuated and filled with argon. This operation was repeated for three times. After completely removing water from the reaction solution, 20 mg of a stannous octoate solution was added, and the reaction solution was further evacuated till no bubbles present therein. The reaction solution was heated to 180° C., to carry out reaction for 6 h. Then, the heating was stopped, and the reaction solution was cooled to room temperature, to which was added 8 ml of dichloromethane. After fully stirring, 400 mL of anhydrous ethyl ether was added to the reaction solution. After fully stirring, the reaction solution was layered by standing, and the subnatant was extracted again with 400 ml of anhydrous ethyl ether, to give a brown liquid product 1-1 10.13 g. $^1$H spectra: $^1$H NMR (CDCl$_3$, δ ppm): δ 5.1-5.2 (m, 16H), δ 4.29 (m, 6H), δ 3.6-3.7 (m, 160 H), δ 1.54-1.58 (m, 64H). Mass spectra, 1683 (M+1).

In the following steps, other biscyanoacrylic acid esters were synthesized according to a method similar to the aforesaid one, with the exception that a different middle segment was added in the synthetic step of compound 2-3.

Synthetic Route:

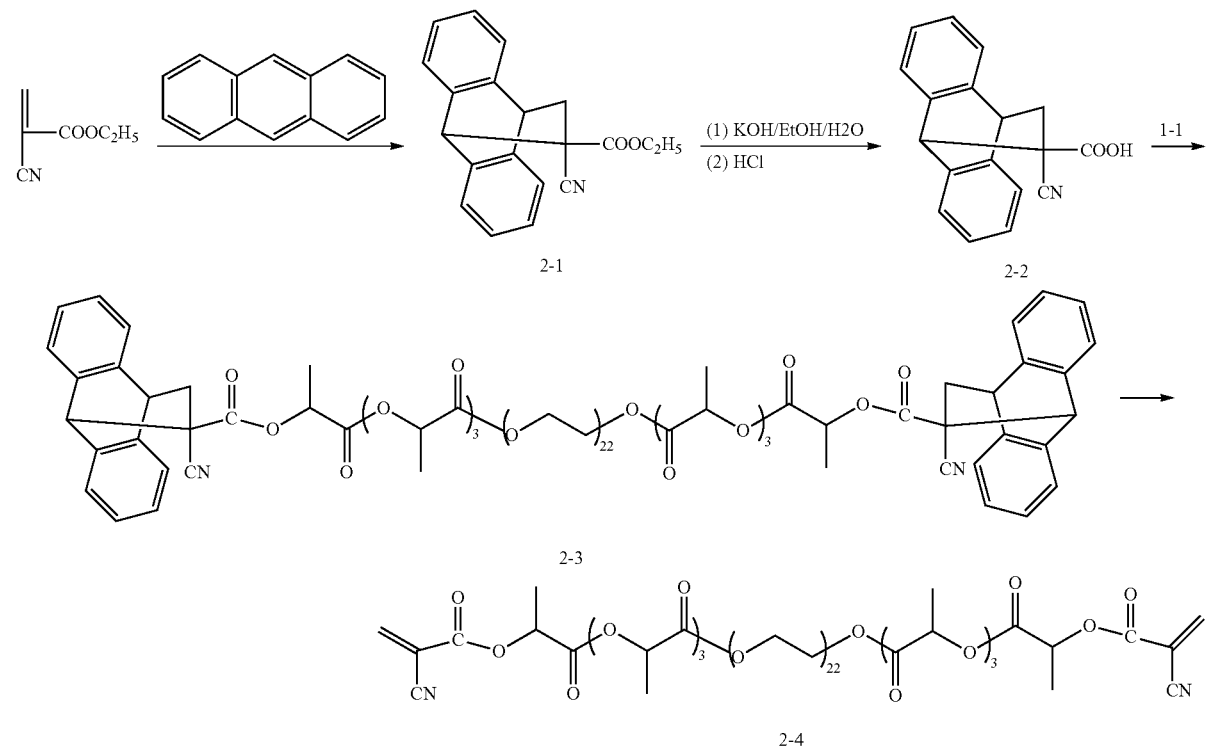

11-Cyano-11-ethoxycarbonyl-9,10-dihydro-9,10-endo-bridged ethylanthracene (2-1)

150 ml of anhydrous benzene was added to a 250 ml three-neck flask, to which were added 60 g (0.48 mol) of ethyl cyanoacrylate and 87 g (0.48 mol) of anthracene under the protection of sulfur dioxide gas, followed by stirring to dissolve. The reaction solution was heated and allowed to reflux 48 h till complete reaction. Then, the reaction solution was cooled in an ice bath, filtered, evaporated to remove the solvent, and recrystallized with ethanol, to give a white solid 2-1 130 g, Yield: 88.4%. H spectra: δ 7.1-7.5 (m, 16H), δ 4.87 (s, 2H), δ 4.43(s,2H), δ 4.15 (m, 4H), δ 2.80 (dd, 2H), δ 2.21 (dd, 2H), δ 1.27 (t, 6H). Mass spectra: 321.1 (M+18, +$NH_4^+$).

11-Cyano-11-carboxy-9,10-dihydro-9,10-endo-bridged ethylanthracene (2-2)

130 g of product 2-1 was dissolved in 400 ml of 95% ethanol, followed by heating and allowing to reflux till complete dissolution. A solution of 3.6 mol/L KOH aqueous solution was dropped, while heating and allowing to reflux for 3 h. The reaction solution was poured into 1500 ml of water, and fully mixed. Then, the mixture was washed with dichloromethane, and adjusted with 6 mol/L hydrochloric acid to pH=2, to precipitate out a solid, which was filtered and dried to give product 1-2 104 g. Yield: 78.8%. H spectra: δ 7.1-7.5 (m, 16H), δ 4.87 (s, 2H), δ 4.43 (s, 2H), δ 2.70 (dd, 2H), δ 2.24 (dd, 2H). Mass spectra: 274.3 (M−1).

Synthesis of dianthra-cyanoacrylic Acid PLA-PEG-PLA Ester (2-3)

2.14 g (0.0078 mol) of product 1-2, 4.80 g (0.0024 mol) of 1-1, 1.48 g (0.0077 mol) of EDCI, 0.11 g (0.0009 mol) of DMAP, and 150 mL of dichloromethane were added to a 250 mL round bottom flask, and reacted at room temperature for 7 h. The reaction mixture was washed with 50 mL of saturated sodium bicarbonate solution, and 50 mL of saturated brine, dried with anhydrous sodium sulfate overnight, concentrated, and then purified by separation on column with a dichloromethane-methanol 50:1 system, to give the product as a yellowish oily liquid 2-1 4.8 g. Yield: 79.5%. $^1$H spectra: $^1$H NMR ($CDCl_3$, δ ppm): δ 7.1-7.5 (m, 16H), δ 5.1-5.2 (m, 16H), δ 4.29 (m, 6H), δ 3.6-3.7 (m, 160 H), δ 1.54-1.58 (m, 64H). Mass spectra: 2163 (M+1).

Synthesis of bis-α-cyanoacrylic Acid PLA-PEG-PLA Ester (2-4)

0.5 g (0.2 mmol) of product 2-3, 0.16 g (1.6 mmol) of maleic anhydride, and 30 mL of xylene were added to a 50 mL flask, and dissolved with stirring. To the solution, 15 mg of phosphorus pentoxide and 7 mg of hydroquinone were added, and heated and allowed to reflux for 6h at a temperature of 140° C. Then, the reaction was stopped, and the reaction solution was cooled to room temperature. Xylene was distilled off under reduced pressure, and the reaction product was dissolved with benzene and distilled for three times. The product was dissolved with benzene, filtered by suction to remove impurities, and then benzene was evaporated to dryness. Finally, the product was dissolved with dichloromethane, and purified by crystallization with anhydrous ethyl ether-dichloromethane, to give a white solid product 2-3.

$^1$H spectra: $^1$H NMR ($CDCl_3$, δ ppm): δ 7.12 (s, 2H), δ 6.71 (s, 2H), δ 5.1-5.2 (m, 16H), δ 4.29 (m, 6H), δ 3.6-3.7 (m, 160 H), δ 1.54-1.58 (m, 64H).

Preparation Example 2

Examples of Other bis-α-cyanoacrylates

The following compounds were synthesized by using a method similar to Example 1, with the use of different middle segments:

Bis-α-cyanoacrylic acid diethylene glycol ester
$^1$H NMR ($CDCl_3$, δ ppm): δ 7.07 (s, 2H), δ 6.67 (s, 2H), δ 4.44 (t, 4H), δ 3.82 (t, 4 H), as a yellowish oily liquid Bis-α-cyanoacrylic acid tetraethylene glycol ester
$^1$H NMR ($CDCl_3$, δ ppm): δ 7.08 (s, 2H), δ 6.65 (s, 2H), δ 4.44 (t, 4H), δ 3.80 (t, 4 H), δ 3.66-3.70 (m, 8H), as a yellowish oily liquid Bis-α-cyanoacrylic acid PEG600 ester
$^1$H NMR ($CDCl_3$, δ ppm): δ 7.08 (s, 2H), δ 6.66 (s, 2H), δ 4.43 (m, 4H), δ 3.68 (m, 54H)

Bis-α-cyanoacrylic acid PEG1000 ester
$^1$H NMR ($CDCl_3$, δ ppm): δ 7.08 (s, 2H), δ 6.71 (s, 2H), δ 4.42-4.44 (m, 4H), δ 3.57-3.80 (m, 90H), as a yellowish oily liquid Bis-α-cyanoacrylic acid PEG2000 ester
$^1$H NMR ($CDCl_3$, δ ppm): δ 7.09 (s, 2H), δ 6.66 (s, 2H), δ 4.42-4.44 (t, 4H), δ 3.57-3.80 (m, 232H), as a white solid Bis-α-cyanoacrylic acid PEG4000 ester
$^1$H NMR ($CDCl_3$, δ ppm): δ 7.08 (s, 2H), δ 6.66 (s, 2H), δ 4.42-4.44 (m, 4H), δ 3.57-3.80 (m, 360H), as a white solid Bis-α-cyanoacrylic acid PEG6000 ester
$^1$H NMR ($CDCl_3$, δ ppm): δ 7.08 (s, 2H), δ 6.71 (s, 2H), δ 4.32 (t, 4H), δ 3.68-3.70 (m, 604H), as a white solid Bis-α-cyanoacrylic acid butanediol ester
$^1$H NMR ($CDCl_3$, δ ppm): δ 7.08 (s, 2H), δ 6.66 (s, 2H), δ 4.34 (t, 4H), δ 1.87-1.89 (m, 4H), as a white solid Bis-α-cyanoacrylic acid octanediol ester
$^1$H NMR ($CDCl_3$, δ ppm): δ 7.06 (s, 2H), δ 6.62 (s, 2H), δ 4.26-4.29 (t, 4H), δ 1.87-1.89 (m, 4H), δ 1.37-1.42 (m, 8H), as a white solid Bis-α-cyanoacrylic acid dodecyl glycol ester
$^1$H NMR ($CDCl_3$, δ ppm): 7.06 (s, 2H), 6.62 (s, 2H), 4.26-4.29 (t, 4H), 1.87-1.89 (m, 4H), 1.37-1.42 (m, 16H), as a white solid.

And, all the products met the purity requirements.

Preparation Example 3

Mono-α-cyanoacrylate

This type of compounds was synthesized by using general methods as reported in literatures ((Li Jingfeng, Sun Xiping, Preparation and Application of α-Cyanoacrylate Adhesives, Chinese Journal of Colloid and Polymer, 1999, 17(3): 33-34; CN 87103468A), i.e., polymerizing a cyanoacetate and an aqueous solution of formaldehyde in the presence of a basic catalyst to form a low molecular weight prepolymer, and then depolymerizing and refining at a high temperature under reduced pressure. Taking n-butyl cyanoacrylate as an example, the chemical reaction formula was described as follows:

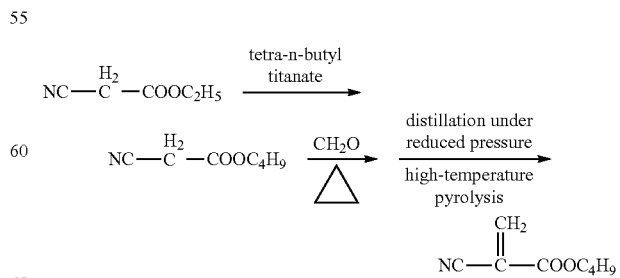

whereby mono-α-cyanoacrylate was obtained.

Example 1

Composition and Preparation of a Formulated Adhesive

The formulation described in this example is a particularly preferred formulation in the present invention

TABLE 1

| | Formula of Example 1 |
|---|---|
| Serial No. | Formula in weight ratio |
| J01 | bis-α-cyanoacrylic acid PEG2000 ester:n-butyl α-cyanoacrylate 1:1 |

Wherein the bis-α-cyanoacrylic acid PEG2000 ester and n-butyl α-cyanoacrylate monomers were synthesized by using methods similar to those disclosed in literatures (U.S. Pat. Nos. 3,975,422, 4,012,402, 4,041,061; CN87103468A), which had been described in the preparation examples.

The concrete preparation method was described as follows:

1. Sterilization: all the vessels used were soaked with acid (0.5 M diluted sulfuric acid) and washed, and then sterilized at a high temperature; n-butyl cyanoacrylate was subjected to aseptic filtration through an organic microporous filtration membrane (Solarbio Co. Ltd.) with a pore size of 0.22 um.

2. Under dry conditions, 5 g of n-butyl cyanoacrylate, and 5 g of bis-α-cyanoacrylic acid PEG2000 ester were added to a vessel, and rapidly shaken with a vortex shaker for 10 min, to give a colorless transparent liquid, i.e., the medical adhesive of Example 1.

3. Storage: the medical adhesive obtained in step 2 was subpackaged in vessels in a dry environment, followed by filling the vessels with an inert gas such as nitrogen and argon; then, the vessels were sealed, and stored in a refrigerator (4° C. or lower); the adhesive could be stored stably for more than three months.

4. Use: the medical adhesive obtained in step 2 was taken directly, or the medical adhesive stored according to step 3 was taken from the low temperature environment and returned to room temperature; the medical adhesive was liquid, at this time, the cyanoacrylate molecules comprised therein were still in the form of non-polymerized monomers; upon contacting the medical adhesive with the application site such as wound or tissue by means of smearing, spraying, dropping and the like, the medical adhesive rapidly polymerized to form a solid polymer and adhered to the tissue. The curing time and degradation property thereof will be further described in the following Examples 3, 4, 5, 6.

Example 2

Compositions and Preparation of Several Formulated Adhesives

According to the formulations shown in Table 2, the medical adhesives comprising different components in different ratios according to the present invention, except for the one obtained in Example 1, could be obtained, wherein the mono-/bis-α-cyanoacrylates were synthesized by using methods similar to those disclosed in the literatures (U.S. Pat. Nos. 3,975,422, 4,012,402, 4,041,061; CN87103468A).

The degradation properties and curing time of the formulated adhesives were described in the following Examples 3 and 4.

TABLE 2

| | Formulas of Example 2 |
|---|---|
| Serial No. | Formulas in weight ratio |
| J02 | bis-α-cyanoacrylic acid PEG2000 ester:n-butyl α-cyanoacrylate 1:5 |
| J03 | bis-α-cyanoacrylic acid PEG2000 ester:n-butyl α-cyanoacrylate 9.1:90.9 |
| J04 | bis-α-cyanoacrylic acid PEG2000 ester:n-octyl α-cyanoacrylate 1:1 |
| J05 | bis-α-cyanoacrylic acid PEG2000 ester:n-octyl α-cyanoacrylate 1:5 |
| J06 | bis-α-cyanoacrylic acid PEG2000 ester:n-octyl α-cyanoacrylate 9.1:90.9 |
| J07 | bis-α-cyanoacrylic acid butanediol ester:n-butyl α-cyanoacrylate 1:5 |
| J08 | bis-α-cyanoacrylic acid octanediol ester:n-butyl α-cyanoacrylate 1:5 |
| J09 | bis-α-cyanoacrylic acid butanediol ester:n-octyl α-cyanoacrylate 1:5 |
| J10 | bis-α-cyanoacrylic acid octanediol ester:n-octyl α-cyanoacrylate 1:5 |
| J11 | bis-α-cyanoacrylic acid (PLA-PEG-PLA) ester:n-octyl α-cyanoacrylate 1:1 |
| J12 | bis-α-cyanoacrylic acid diethylene glycol ester:n-butyl α-cyanoacrylate 1:1 |
| J13 | bis-α-cyanoacrylic acid tetraethylene glycol ester:n-octyl α-cyanoacrylate 1:1 |
| J14 | bis-α-cyanoacrylic acid PEG600 ester:n-butyl α-cyanoacrylate 1:1 |
| J15 | bis-α-cyanoacrylic acid PEG 1000 ester:n-octyl α-cyanoacrylate 1:1 |
| J16 | bis-α-cyanoacrylic acid PEG4000 ester:n-octyl α-cyanoacrylate 1:1 |
| J17 | bis-α-cyanoacrylic acid PEG2000 ester:n-butyl α-cyanoacrylate 5:1 |

The preparation methods of the formulated adhesives were the same as the preparation method of formulated adhesive J01 in Example 1, and all the resultant medical adhesives were uniform, colorless or yellowish transparent liquids at room temperature. Upon contacting with skin and living tissue, the medical adhesives rapidly polymerized to form a solid polymer, and generate adhesion.

Example 3

Test of Curing Time of Formulated Adhesives

Test Method: The medical adhesives of different formulations in Examples 1 and 2 were respectively dropped in a small amount on the surface of one piece of pigskin at room temperature, and the other piece of pigskin was rapidly lapped thereon; the two pieces of pigskin were respectively pulled in opposite directions, to test the adhesion between them. The duration starting from the generation of adhesion between the two pieces of pigskin to the complete cure of the liquid adhesive between the two pieces of pigskin after lapping for a certain time was designated as the curing time.

The test results showed that the curing time of both the formulated adhesives in Example 1 and 2 were about 5 to 15 seconds. This prompted that the medical adhesive of the present invention could meet the requirement in actual operation in terms of curing time, which did not produce a slow hemostatic effect due to a too long curing time, nor had the problem of unable to operate due to a too short curing time. Under the same conditions, the curing time of n-butyl cyanoacrylate as control was also 5 to 15 seconds.

Example 4

Test of Degradation Property

Test Method: The medical adhesives Nos. J1 to J11 in Examples 1 and 2, each 100 mg, were respectively dropped on a glass plate 2.5×3 cm. After fully cured, the medical adhesives were dried in vacuo and weighed to obtain their initial weights. The glass plate was placed in a conical flask filled with a 0.1 M phosphate buffer at pH 7.2-7.4 (PBS buffer, $K_2HPO_4.3H_2O$ 1.85 g/L, $KH_2PO_4$ 0.24 g/L, NaCl 8.00 g/L, KCl 0.20 g/L), or bovine serum (Beijing Yuanheng Jinma Biotechnology Development Co., Ltd., newborn bovine serum). The conical flask was placed on a thermostatic shaking table at 37.5° C. for degradation. After 14 days, the residual solids were weighed. The results were used to evaluate the degradation properties. That is to say, the less the residual solid was, the more the degraded amount was, and the greater the degradation of the adhesive bond was. Three samples were tested in parallel, and the obtained data were averaged. The results were shown in Table 3 below.

TABLE 3

Test results of degradation properties

| Serial No. | Residual solids % in PBS |
| --- | --- |
| J01 | 38.44 |
| J02 | 85.87 |
| J03 | 92.22 |
| J04 | 58.35 |
| J05 | 89.97 |
| J06 | 92.69 |
| J07 | 94.89 |
| J08 | 95.45 |
| J09 | 95.44 |
| J10 | 95.00 |
| J11 | 34.63 |
| Control (n-butyl cyanoacrylate) | 95.74 |

As could be seen from the above table, the formulated adhesives Nos. J01, J02, J04, J05, J11 and the like all had a residual solid percentage that was significantly lower than that of the control (95.74%). This indicated that their degradation properties were significantly improved. As could also be seen, different types of mono-/bis-esters, and different ratios thereof both exerted different influences on the degradation rate. Therefore, the above results also reflected the design concept of the present invention, i.e., selecting appropriate composition and ratio of mono-/bis-esters to obtain medical adhesives having preferable degradation properties.

With comprehensive consideration of various factors including synthesis, product's purity and the like, the particularly preferred formulation of the present invention is No. J01, i.e., bis-α-cyanoacrylic acid PEG2000 ester:n-butyl α-cyanoacrylate 1:1.

The degradation properties in bovine serum were compared between the polymerized adhesive bond of formulation J01 and control (n-butyl cyanoacrylate, the main ingredient comprised in commercially available cyanoacrylate medical adhesive, as synthesized independently in laboratory) according to the method provided in this example (cf. Table 4). The results indicated that the adhesive bond of No. J01 had a residual solid percentage (0.33%) that was far lower than that of the control (91.39%). This again demonstrated the good degradation property of the formulated adhesive No. J01.

Further accelerated degradation test was carried out in a 0.1 N NaOH solution. The operation method was the same as that provided in this example, with the use of formulated adhesive J01 and the control as samples. The time point when the adhesive bond completely disappeared to the naked eye was regarded as the complete degradation time. The degradation time was shown in Table 4. The degradation rate of the adhesive bond polymer in formulated adhesive J01 was significantly faster than that in the control.

TABLE 4

Degradation results in bovine serum, NaOH solution

| | Formula adhesive J01 | Control |
| --- | --- | --- |
| Degradation for 14 days in bovine serum | Residual solids 0.33% | Residual solids 91.39% |
| Degradation in NaOH | Solids completely disappeared after 7 h | Solids completely disappeared after 4 days |

Example 5

Analysis of Degradation Products of Formulated Adhesive J01

The PBS solution in which the particularly preferred formulated adhesive J01 of the present invention, as described in Example 4, had been degraded for 14 days was evaporated to dryness. The degradation products of formulated adhesive J01 as comprised in the solution were tested by using molecular exclusion chromatodiagramy (GPC), $^1$H-NMR and bio-mass spectrometry.

FIG. 2 was a GPC diagram of J01, showing a peak time and the corresponding approximate molecular weight of 23.918 min/2610 D. The degradation product appeared in the solution, with a molecular weight of less than 3,000, which indicated that the degradation of the polymer indeed occurred. The fragments having such a molecular weight could be absorbed by human body and discharged.

Figure 3:
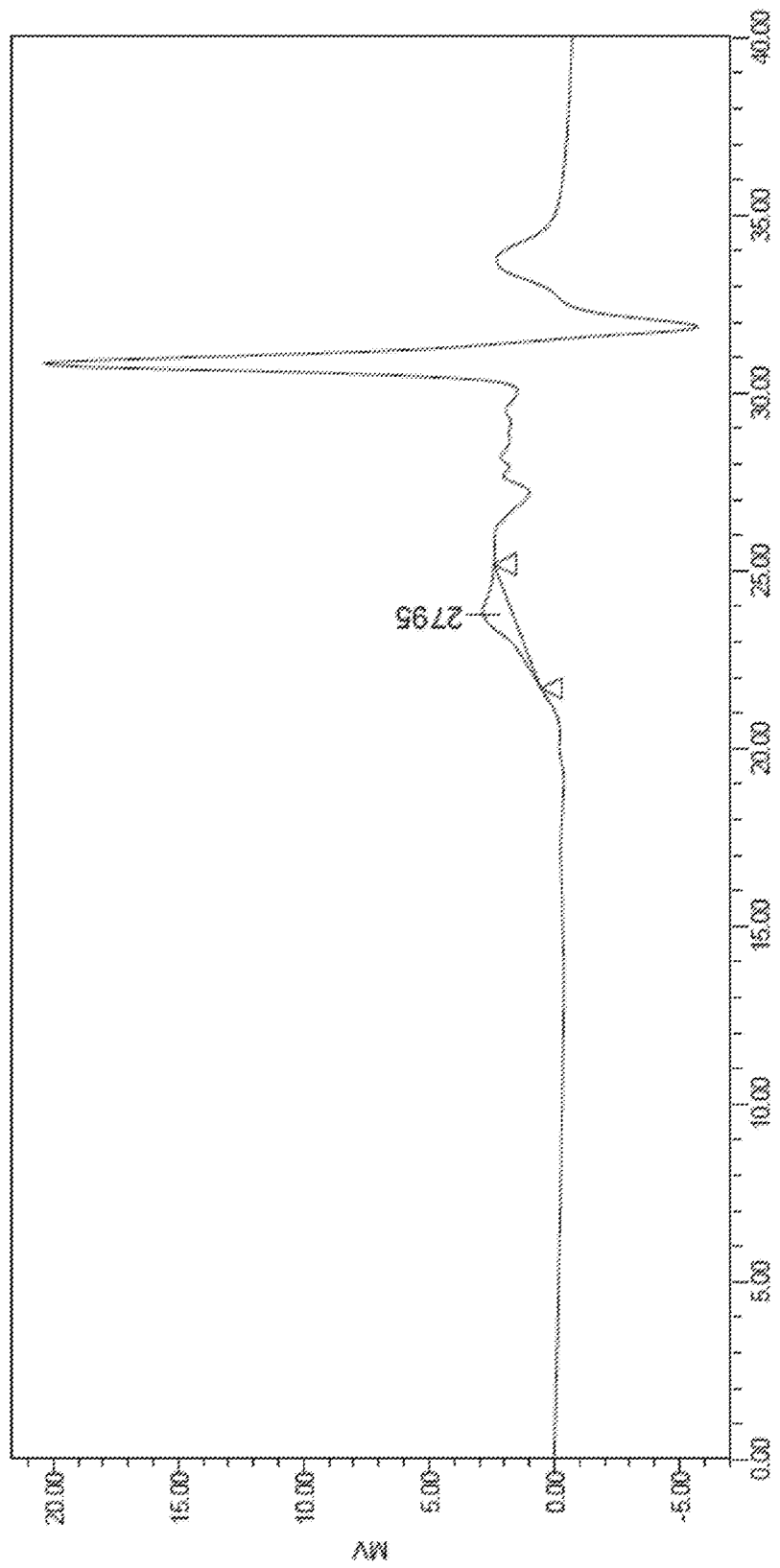
FIG. 3, a GPC diagram of residual solid of polymer No. J01.

The residual solid in the PBS solution was dissolved by using tetrahydrofuran (THF), and analyzed by using GPC (FIG. 3). It was discovered that the molecular weight of the solid was also below 4,000. In comparison with the fact that the polymer (three-dimensional polymer, which cannot be dissolved as a whole) before degradation was hardly dissolved in THF, it indicated that the three-dimensional structure of the polymer as a whole had been destroyed, and the residual non-completely-degraded adhesive bond, which comprised short segments having a molecular weight of less than 4,000, i.e., short segments of linear or branched polymers, could be further degraded and absorbed.

Figure 4:
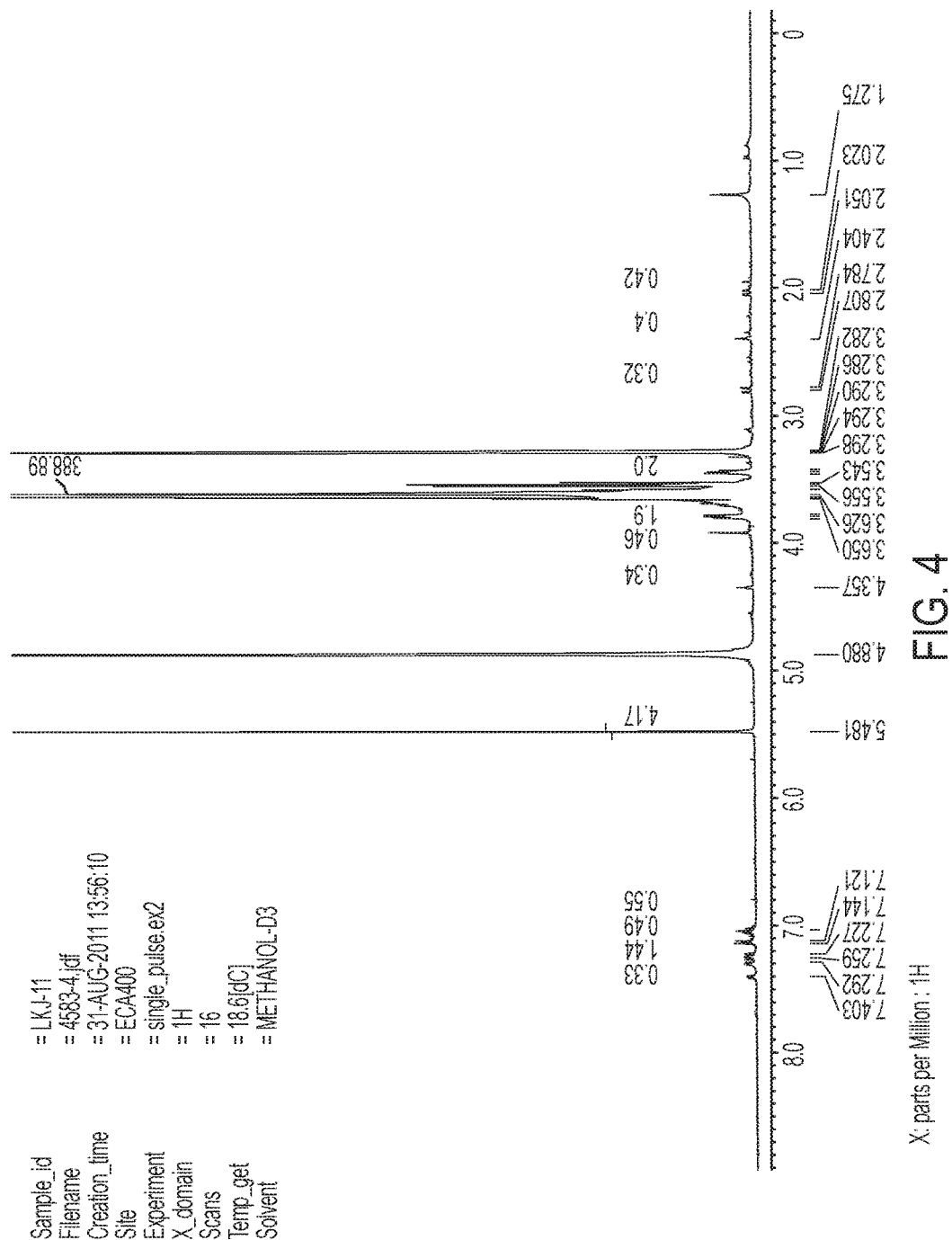
FIG. 4, $^1$H-NMR spectrum of degradation product of polymer No. A.
Figure 5:
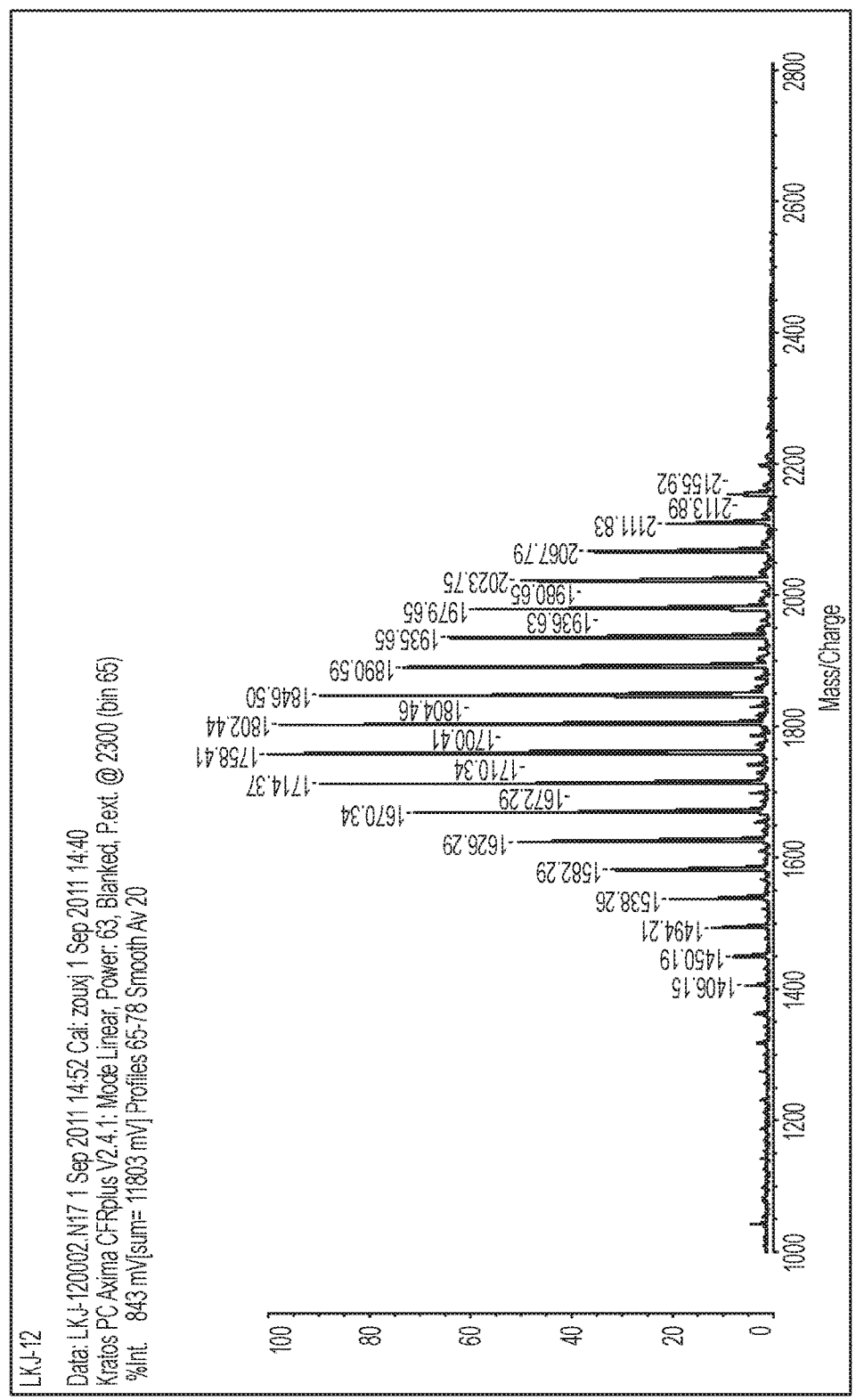
FIG. 5, bio-mass spectrum of degradation product of polymer No. A.

FIGS. 4 and 5 are respectively $^1$H-NMR spectrum and bio-mass spectrum of degradation product of polymer No. J01. From the Figures, it could be seen that the degradation product not only had the characteristic absorption peak of PEG2000 molecule, but also comprised a small amount of polycyanoacrylate fragments. The results further indicated that the polymer degraded via ester linkage positions into PEG segments and short segments of polycyanoacrylate, all the fragments having a molecular weight of less than 3,000.

Example 6

Intestinal Adhesion Degradation Test in Rats

Two groups of adult rats, each six, were taken. The abdominal cavity was opened, a section of small intestine was lifted and stretched out with a biodegradable thread, approximately 1 cm away from the body, and in an inverted "U" shape. The particularly preferred formulation J01 of the present invention and the control (n-butyl cyanoacrylate), each 20 uL, were dripped along the thread on the surface of the small intestine. After the adhesive bond was completely cured and the small intestine was adhered together (about 1 minute), the small intestine was put back into the abdominal cavity, followed by suturing. Normal healing time of biological tissue was about 7-10 days. After 2 weeks, the small intestine was stretched out again, for observing the changes of the small intestine per se and the adhesive bond. The results were shown in FIG. 6. It could be seen that the color and shape of the small intestine adhered with the formulated adhesive J01 substantially recovered to normal state, while no significant solid adhesive bond being observed. This indicated that the adhesive bond was well degraded, and did not cause significant changes to the intestinal tissue. In contrast, as to the small intestine adhered with the control adhesive, it was observed that partial intestinal body was still adhered together, and the intestinal tissue significantly had hyperplasia and significantly became thicker. This indicated that the long-term presence of the control adhesive in the body, as it could not be degraded, resulted in foreign body reaction, and caused hyperblastosis.

Figure 6:
FIG. 6, comparison results of degradation experiments in mice.

FIG. 6 is a picture of intestine fragments in this example.

Example 7

TEM Test 20 mg of adhesive (A, n-butyl cyanoacrylate as control; B, formulated adhesive J01 (bis-α-cyanoacrylic acid PEG2000 ester:n-butyl cyanoacrylate 1:1, i.e., the formulated adhesive in Example 1) was dissolved in 1 mL of redistilled acetone, to obtain a homogeneous solution, which was diluted by 100-fold. 0.5 mL of the dilution was taken and mixed with 0.5 mL of deionized water. Acetone was distilled off, and water was supplemented till 1 mL, to obtain a 0.1 mg/mL dilution. 15 uL of the dilution was dropped on a copper web-like of electron microscopy, and settled for 15 min. Then, water was removed by adsorption with filter paper. After staining with 5 uL of phosphotungstic acid for 2 min, the samples were observed by transmission electron microscopy. The results showed that n-butyl cyanoacrylate A, under this condition, formed a relatively solid and dense microsphere structure (see FIG. 7-A), whereas the formulated adhesive J01 presented a relatively loose irregular shape with pore structure (see FIG. 7-B). This further demonstrated that, due to the addition of bis-α-cyanoacrylic acid PEG2000 ester, the polymer formed by the formulated adhesive J01 had a relatively loose adhesive bond structure, which was more favorable for the degradation.

Example 8

Comparison Test of Flexibility of Adhesive Bonds

Five adult rats were unhaired on the back, and subjected to abdominal anesthesia. On their backs, four formulated adhesives were uniformly smeared in turn about 2 cm² each (A, n-butyl cyanoacrylate as control; B, bis-α-cyanoacrylic acid PEG2000 ester:n-butyl cyanoacrylate 1:5 (J02); C, bis-α-cyanoacrylic acid PEG2000 ester:n-butyl cyanoacrylate 1:1 (J01); D, bis-α-cyanoacrylic acid PEG2000 ester:n-butyl cyanoacrylate 5:1 (J17)). The rats were bred respectively with normal diet, and the adhesive bonds presented on the skin surface were observed. The results (see FIG. 8) showed that the adhesive bonds obtained by the polymerization of the formulated adhesives B, C and D all exhibited better flexibility to different degrees than the control. The control adhesive bond was relatively hard, presenting rigid wrinkles on the skin surface of the rats, and it was easy to fall off as the rats moved. In contrast, the adhesive bonds obtained by the polymerization of the formulated adhesives were relatively soft, presenting no rigid wrinkles on the skin surface of the rats, and the adhesive bonds ware not easy to fall off as the skin bent.

Example 9

Adhesion Test of Skin Incision Injury of Rats/Guinea Pigs

Five adult rats and five guinea pigs were unhaired on the back, and subjected to abdominal anesthesia. After the back was disinfected, a longitudinal incision of about 2 cm in length was cut about 1 cm next to the dorsal line, deep to muscular layer. After hemostasis, the skin incision was fit tightly, then the particularly preferred formulated adhesive J01 of the present invention was rapidly smeared uniformly on the wound skin surface, and fixed for about 30 seconds, whereby the wound was well adhered together. On the other side of the back, an incision of the same size was cut, and the wound was treated in the same way with the control adhesive n-butyl cyanoacrylate. Finally, the operative sites were bandaged using gauze. FIG. 9 and FIG. 10 respectively showed the conditions of wound healing in the rats and guinea pigs 1 day and 7 days after operation, wherein the left wound was treated with the formulated adhesive of Example 1, and the right wound was treated with the control adhesive. FIG. 8 showed a comparative example, wherein the wound was not treated. As observed over time, the wounds treated with both the formulated adhesive of the present invention and the control adhesive were well closed, no wound dehiscence and secondary bleeding would occur with daily exercise of rats and guinea pigs, and no infection occurred at the adhered sites. Moreover, the formulated adhesive J01 had significantly better adhesive bond flexibility than the control. One week after the test, the treated animals exhibited good wound healing, with substantially no significant presence of the wound. In contrast, the non-treated wound recovered slowly, and was still exposed in dehiscence. It was observed in the test that some animals even died because of wound infection.

Example 10

Adhesion Test of Skin and Stomach Incision Injury of Dog

Adult test dogs (purchased from Experimental Animal Center of Academy of Military Medical Sciences) were unhaired on the neck and back, and disinfected. A longitudinal incision of about 4 cm in length was cut on the left side, deep to muscular layer. After hemostasis, the incision was fit tightly, and sutured in two stitches, then the formulated adhesive in Example 1 of the present invention was rapidly smeared uniformly on the wound skin surface, and fixed for about 30 seconds, whereby the wound was well adhered together. On the other side of the same position, an incision of the same size was cut, and also sutured in two stitches. Then, the wound was treated in the same way with n-butyl cyanoacrylate. As observed over time, after one week, the wound of the dog exhibited good healing, no wound dehiscence and secondary bleeding occurred, and no infection occurred at the adhered sites. Moreover, the formulated adhesive had better adhesive bond flexibility than n-butyl cyanoacrylate.

The similar incision injury adhesion test was also applied to the assisted suture of stomach injury of dog. In concrete, after a surgical wound of about 2 cm in the dog's stomach had been sutured in two stitches using an ordinary suture silk, the formulated adhesive J01 was used for assisted adhesion. The dog was in good condition after operation. In contrast, after the previous operation which was conducted under the same conditions by only suturing the stomach without the use of any adhesive, the dog might die because the suture silk was burned out by gastric acid.

Example 11

Degradation Test after Intramuscular Injection

Twenty healthy rabbits (purchased from Experimental Animal Center of Academy of Military Medical Sciences) were anaesthetized i.v. with 30 mg/kg pentobarbital. An incision of 10 mm was cut on the skin lateral to the hind legs to expose muscle, without destroying the dermis, and then 30 uL of adhesive was intramuscularly injected. The left and right legs of the same rabbit were respectively injected with the formulated adhesive in Example 1 and the control adhesive n-butyl cyanoacrylate. After suture of the skin, the rabbits were fed normally. The skin was incised 1 day, 14 days and 75 days after the operation respectively, to observe the state and degradation of the adhesives. After 75 days, the injected sites were subjected to histopathological observation.

Figure 12:
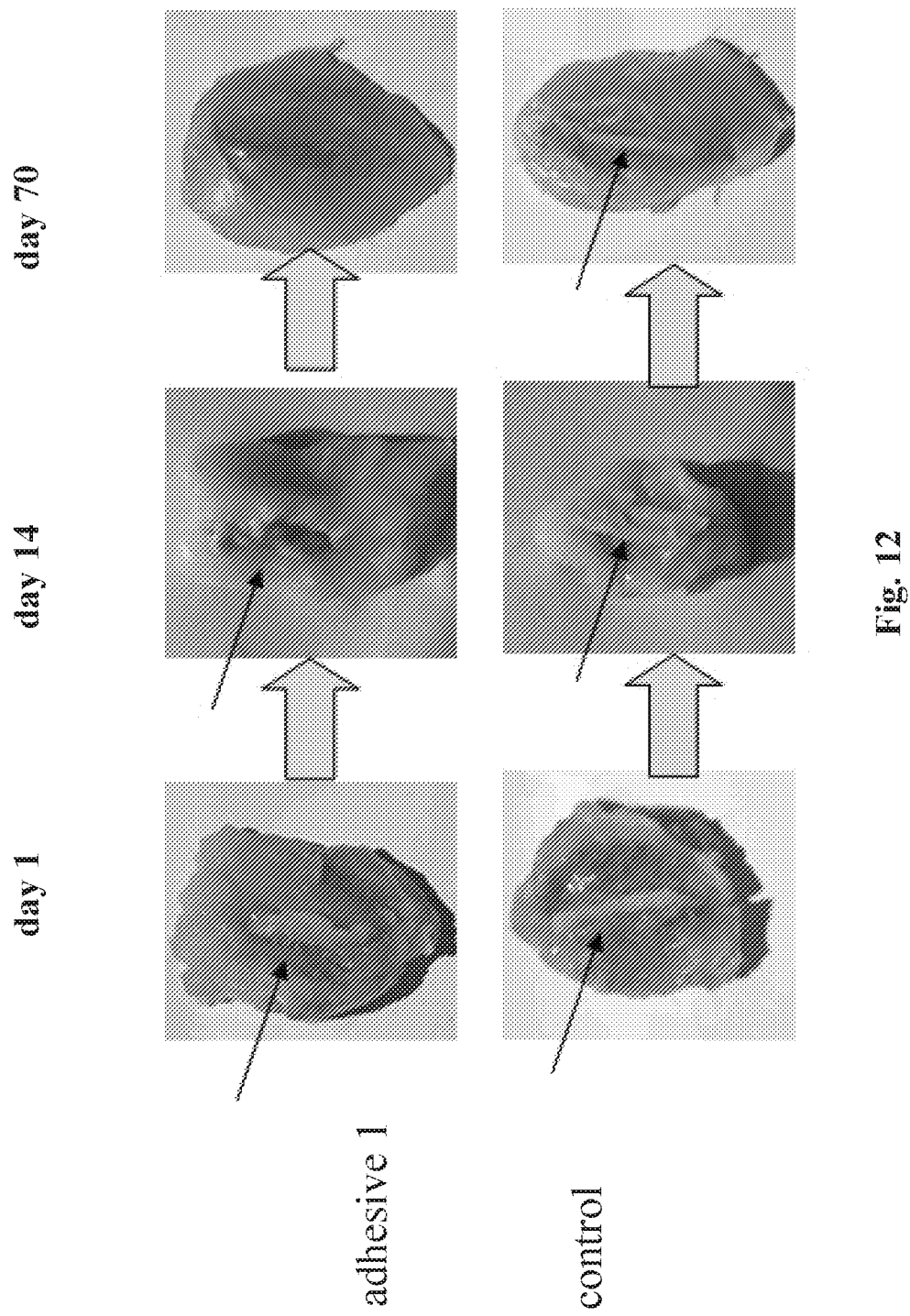
FIG. 12, experimental result diagram of degradation in rabbits after intramuscular injection.

The results were as follows:

The particularly preferred formulated adhesive J01 of the present invention and the control adhesive, after being injected into muscle, rapidly polymerized to produce a solid polymer in the muscle. After one day, samples were taken by dissection. It was observed that the adhesive bonds in both groups were in the form of gelosis, and the adhesive bond in the control group was harder and bone-like. The samples taken after 14 days showed that the adhesive bond of the J01 group became soft and was partially absorbed as the adhesive bond dissolved, whereas the adhesive bond in the control group did not dissolve, and was substantially unchanged in hardness. The samples taken after 75 days showed that the gelosis of the formulated adhesive J01 disappeared completely to the naked eyes, and there were only particulate residues in the biopsy. The results revealed that: the adhesive bond of the J01 group was degraded and absorbed by tissue, and could be completely absorbed by tissue over time; in contrast, the control adhesive bond after 75 days was visually the same as that after 14 days, and still showed bone-like residues, hard texture (see FIG. 12).

Example 12

Intestinal Skyrocketing Compression Test in Rats

Twenty SD rats (purchased from Experimental Animal Center of Academy of Military Medical Sciences) were anaesthetized by intraperitoneal injection of 45 mg/kg sodium pentobarbital, and unhaired on the abdomen. The abdominal cavity was opened, and a section of small intestine 45 mm was taken out. One end of the small intestine was ligated with a silk thread, and the other end was cut to make a small incision, which was then connected to a three-way tube in connection with a pressure gauge and a tension transducer. A syringe needle 2 mm in diameter was used to open a small hole in the small intestine. After cleaning off drainage with cotton, the small hole was rapidly closed by smearing 5 uL medical adhesive, and then test was conducted after standing for 3 min. The pressure was gradually increased until the small intestine was damaged with air leakage through the small hole. The pressure value at this point was just the maximum tolerable pressure. There were seven animals per group, and the average value and variance were calculated.

Test results: the pressure value in the group with the particularly preferred formulated adhesive J01 of the present invention was 118.59±37.44 mmHg, and that in the control group was 120.22±26.81 mmHg. There was no significant difference between the two groups.

Moreover, both the pressure values were far greater than the normal intestinal peristalsis pressure (about 15 mmHg) of rats. The results indicated that the formulated adhesive J01 achieved a good sealing and adhering effect to intestinal hole in this test model, and could provide the desired adhesive strength in the case of treating small intestinal tissue using medical adhesive.

Example 13

Skin Irritation Test

Four healthy rabbits, 24 h before the test, were unhaired with sodium sulfide at both sides of dorsal line, to obtain an unhaired area of about 8×8 $cm^2$. 0.1 mL of the particularly preferred formulated adhesive J01 of the present invention and the control adhesive n-butyl cyanoacrylate were respectively applied to four different circular areas of 2.5 cm in diameter, and smeared slowly and carefully till uniform. Thereafter, the smeared areas were covered with two layers of gauze, and fixed with non-irritating tape and bandage. After 4 hours, the test samples were removed with warm water. Then, the skin reactions were observed at the $1^{st}$, $24^{th}$, $48^{th}$, and $72^{nd}$ h respectively. The evaluation was conducted in terms of skin erythema, edema reaction integral and irritation strength. After completion of the test, the smeared skin was subjected to biopsy.

The test results: no significant skin irritation was observed in the J01 group. After removing the adhesive bond which had been present on the surface of rabbit skin for a period of time, as observed at the $1^{st}$, $24^{th}$, $48^{th}$, and $72^{nd}$ h respectively, the skin in the test area did not exhibit any symptom of skin erythema and/or edema. The results of the biopsy: the skin biopsy of the J01 group exhibited an integral epidermal structure, with clear cuticle. The cells in epidermal accessory structures including dermis follicles, sebaceous glands and the like were arranged in neat rows, and no proliferation was observed in the structures including vascular tissue, collagen fibers and the like. The results were consistent with those of normal tissue.

Example 14

Acute Toxicity Test

Only male mice were involved in gavage group. They were subjected to fasting 24 hours before the administration, while the room temperature being held at about 24° C. A polymer powder of the particularly preferred formulated adhesive J01 of the present invention was suspended using 0.5% CMC aqueous solution for gavage. The gavage volume of mice was 50 mL/kg (maximum tolerable volume). The lethal dose range was estimated in advance according to the test with a small number of animals. No toxic reaction occurred in the dose range of 1-2 g/kg. Eventually, the maximum tolerable dose of 10 g/kg was administered. After observed for 14 days after administration, the mice were killed alive, for visual observation of pathological changes, and statistics of dynamic changes in animal body weight.

No acute toxicity of the J01 adhesive bond was observed. After administered by gavage with a crushed powder of the J01 adhesive bond in the maximum tolerable dose of 10 g/kg, the mice did not exhibit any toxic reaction, and their body weights increased over time, with no significant difference as compared with the normally fed control group. When the mice were killed alive after 14 days, no abnormality was visually observed.

Example 15

Antibacterial Test

Bacteria (*Staphylococcus aureus, Bacillus subtilis, Escherichia coli*, the bacterial strains were donated by Dr. Wang Chenhong from Beijing Institute of Pharmacology and Toxicology) were spread on an agar medium. 10 uL of the particularly preferred formulated adhesive J01 of the present invention was dropped on the surface of the medium, and naturally polymerized. After complete cure of the adhesive bond, the medium was thermostatically incubated at 37° C. for 18 h, and then visually observed.

The adhesive bond formed by the J01 adhesive produced a significant inhibition zone directed to *Staphylococcus aureus, Bacillus subtilis* and *Escherichia coli*, which indicated that it had antibacterial effects. Wherein, the inhibition zone directed to *Staphylococcus aureus* and *Bacillus subtilis* (belonging to gram-positive bacteria) was larger, and the effect was more obvious.

The invention claimed is:
1. A medical adhesive comprising a mono-α-cyanoacrylate and a bis-α-cyanoacrylic acid diol ester in a weight ratio of 1:1, wherein:
   1) the bis-α-cyanoacrylic acid diol ester is bis-α-cyanoacrylic acid PEG2000 ester and the mono-α-cyanoacrylate is n-butyl α-cyanoacrylate;
   2) the bis-α-cyanoacrylic acid diol ester is bis-α-cyanoacrylic acid PEG2000 ester and the mono-α-cyanoacrylate is n-octyl α-cyanoacrylate; or
   3) the bis-α-cyanoacrylic acid diol ester is bis-α-cyanoacrylic acid PEG600 ester and the mono-α-cyanoacrylate is n-butyl α-cyanoacrylate.
2. The medical adhesive according to claim 1, wherein the mono-α-cyanoacrylate is n-butyl α-cyanoacrylate and the bis-α-cyanoacrylic acid diol ester is bis-α-cyanoacrylic acid PEG2000 ester.
3. The medical adhesive according to claim 1, further comprising one or more adjuvants selected from the group consisting of
   a) a plasticizer selected from the group consisting of polyethylene glycol ester, end-capped polyester, butyl stearate, lauric acid, dioctyl glutarate, triglyceride, dioctyl oxalate, triethyl phosphate, acetyl tributyl citrate, and combinations thereof;
   b) a thickener selected from the group consisting of polycyanoacrylate, polylactic acid, polyglycolic acid, polycaprolactone, polyacrylic acid alkyl ester, polymethacrylic acid alkyl ester, and combinations thereof;
   c) a preservative selected from the group consisting of potassium sorbate, sodium benzoate, sorbic acid, chlorocresol, and combinations thereof;
   d) a coolant;
   e) a fiber reinforced material selected from the group consisting of natural rubber and synthetic rubber;
   f) a stabilizer including an anionic stabilizer and a free radical stabilizer, wherein the anionic stabilizer is at least one selected from the group consisting of metaphosphoric acid, maleic acid, maleic anhydride, alkyl sulfonic acid, phosphorus pentoxide, iron (III) chloride, antimony oxide, 2,4,6-trinitrophenol, thiol, alkyl sulfonyl, alkyl sulfone, alkyl sulfoxide, alkyl sulfite, sultone, sulfur dioxide, and sulfur trioxide; and the free radical stabilizer is at least one selected from the group consisting of hydroquinone, catechol and derivatives thereof;
   g) a colorant selected from the group consisting of dyes and pigments, and including at least one selected from the group consisting of PGA microfibrils, collagen microfibrils, cellulose microfibrils, and olefinic microfibrils;
   h) a biocompatible agent including sodium bisulfate; and
   i) a polymerization or crosslinking initiator or accelerator comprising molecules including at least one selected from nucleophilic functional groups, organics and inorganics.
4. A method comprising the steps of:
uniformly mixing a mono-α-cyanoacrylate and a bis-α-cyanoacrylic acid diol ester to form a medical adhesive in which the mono-α-cyanoacrylate and the bis-α-cyanoacrylic acid diol ester are in a weight ratio of 1:1, wherein:
   1) the bis-α-cyanoacrylic acid diol ester is bis-α-cyanoacrylic acid PEG2000 ester and the mono-α-cyanoacrylate is n-butyl α-cyanoacrylate;
   2) the bis-α-cyanoacrylic acid diol ester is bis-α-cyanoacrylic acid PEG2000 ester and the mono-α-cyanoacrylate is n-octyl α-cyanoacrylate; or
   3) the bis-α-cyanoacrylic acid diol ester is bis-α-cyanoacrylic acid PEG600 ester and the mono-α-cyanoacrylate is n-butyl α-cyanoacrylate.
5. A method according to claim 4, further comprising placing the medical adhesive in an environment having a temperature of 4° C. or lower, and storing the medical adhesive in insulation from moisture.
6. A method according to claim 4, further comprising contacting the medical adhesive with a wound site to be treated by smearing, spraying, or dropping the medical adhesive on the wound site.
7. A medical adhesive polymer, said medical adhesive polymer being obtained by crosslinking copolymerization of a medical adhesive under the action of anions, wherein the medical adhesive comprises a mono-α-cyanoacrylate and a bis-α-cyanoacrylic acid diol ester in a weight ratio of 1:1, wherein:
   1) the bis-α-cyanoacrylic acid diol ester is bis-α-cyanoacrylic acid PEG2000 ester and the mono-αcyanoacrylate is n-butyl α-cyanoacrylate;
   2) the bis-α-cyanoacrylic acid diol ester is bis-α-cyanoacrylic acid PEG2000 ester and the mono-α-cyanoacrylate is n-octyl α-cyanoacrylate; or

3) the bis-α-cyanoacrylic acid diol ester is bis-α-cyanoacrylic acid PEG600 ester and the mono-α-cyanoacrylate is n-butyl α-cyanoacrylate; and the anions are —OH or —NH$_2$ in blood, body fluids, tissues, skin, or a combination thereof.

8. The medical adhesive according to claim 1, wherein the mono-α-cyanoacrylate is n-octyl α-cyanoacrylate, and the bis-α-cyanoacrylic acid diol ester is bis-α-cyanoacrylic acid PEG2000 ester.

9. The medical adhesive according to claim 1, further comprising one or more biological agents or therapeutic agents selected from the group consisting of anti-inflammatory analgesics, sedatives, local anesthetics, non-steroidal anti-inflammatory agents, antiallergic agents, anti-ulcer agents, antibiotics, antimicrobial agents, antiviral agents, antifungal agents, immunity inhibitors, naturally derived proteins, genetically engineered proteins, polysaccharides, glycoproteins, lipoproteins, oligonucleotides, polypeptide drugs, antibodies, antigens, chemotherapeutics, coagulant agents, hemostatic agents, coagulation factors, tissue factors, collagen, gelatin, vasopressin, plasminogen activator inhibitors, platelet activators and synthetic peptides having hemostatic activity.

10. The medical adhesive according to claim 1, further comprising a pharmaceutically acceptable excipient.

11. The medical adhesive according to claim 1, wherein the bis-α-cyanoacrylic acid diol ester is bis-α-cyanoacrylic acid PEG600 ester and the mono-α-cyanoacrylate is n-butylα-cyanoacrylate.

\* \* \* \* \*